(12) United States Patent
Jakobsen et al.

(10) Patent No.: US 6,436,653 B1
(45) Date of Patent: Aug. 20, 2002

(54) METHOD FOR INTRODUCTION OF REPORTER GROUPS INTO BACTERIAL LIPOPOLYSACCHARIDE-DERIVED CARBOHYDRATES AND THE SUBSEQUENT COUPLING OF SUCH DERIVATIVES ONTO SOLID SURFACES

(75) Inventors: Mogens Havsteen Jakobsen, Vanlose; Ulrik Boas, Copenhagen; Eva Irene Stenbaek Jauho, Copenhagen; Peter M. H. Heegaard, Copenhagen, all of (DK)

(73) Assignee: Exiqon A/S, Vedbaek (DK)

( * ) Notice: Subject to any disclaimer, the term of this patent is extended or adjusted under 35 U.S.C. 154(b) by 0 days.

(21) Appl. No.: 09/460,543

(22) Filed: Dec. 14, 1999

Related U.S. Application Data

(60) Provisional application No. 60/116,280, filed on Jan. 19, 1999.

(30) Foreign Application Priority Data

Dec. 15, 1998 (DE) ......................................... 1998 01655

(51) Int. Cl.$^7$ ............................................. G01N 33/569
(52) U.S. Cl. ..................... 435/7.35; 435/7.32; 436/529
(58) Field of Search .......................... 436/529; 435/7.32, 435/7.35

(56) References Cited

FOREIGN PATENT DOCUMENTS

| DE | 19621488 A1 | 12/1997 |
|----|-------------|---------|
| EP | 0107119 A1 | 10/1983 |
| EP | 0504202 B1 | 5/1995 |
| WO | WO 96/22534 | 7/1996 |
| WO | WO 96/31557 | 10/1996 |
| WO | WO 96/40225 | 12/1996 |

OTHER PUBLICATIONS

Japanese Patent Abstract JP02242448 A—Bio Material Kenkyusho KK.
Meikle et al., *Glycoconjugate 1*, 7:207–218 (1990).
Brade et al., *FEMS Immunology and Medical Microbiology*, 8:27–42 (1994).
Svenson et al., *Journal of Immunology*, vol. 120, No. 5, 1750–1757 (1978).
Gupta et al., *Infection and Immunity*, vol. 63, No. 8, 2805–2810 (1995).
Parlesak et al., *Journal of Chromatography A*, 711, 277–288 (1995).
Jennings et al., *Infection and Immunity*, vol. 43, No. 1, 407–412 (1984).
Cryz, Jr, et al., *Vaccine*, vol. 13, No. 5, 449–453 (1995).
Chernyak et al., *Glycoconjugate J*, 7:111–120 (1990).
Fattom et al., *Infection and Immunity*, 584–589, (1992).
Garbau–Jaureguiberry et al., *J. Med. Chem.*, 35, 72–81 (1992).
Flynn et al., *Biotechniques Euro Edition*, 33–38 (1996).
C. Raetz, *American Society for Microbiology*, vol. 1, 2$^{nd}$ Ed., 1035–1063 (1996).
Koerge et al., *Journal of Immunoassay* 6(4), 391–407 (1985).
Poster at 78$^{th}$ Annual Meeting of the CRWAD, Chicago, IL, Nov. 10 and 11, 1997.
Poster at 29$^{th}$ Ann. Meeting of the Scandinavian Society for Immunology, Copenhagen, Denmark Jun. 10–14, 1998.
Poster at 3$^{rd}$ Int. Symp. on the Epidemiology and Control of Salmonella in Pork, Washington, DC, Aug. 5–7, 1999.
Goldman et al., *Eur. J. Biochem.*, vol. 107, 145–153 (1980).
Beuvery et al., *Develop. Biol. Standard*, vol. 63, 117–128 (1986).
Lambden et al., *Journal of Immunological Methods*, vol. 48, 233–240 (1982).
Munford et al., *Infection and Immunity*, vol. 26. No. 1, 42–48 (1979).
Hicthcock et al., *Journal of Bacteriology*, vol. 166, No. 3, 699–705 (1986).
Svenson et al., *Journal of Virology*, vol. 32, No. 2, 583–592 (1979).
van de Wiel et al., *Vaccine*, vol. 5, 33–38 (1987).
Elkins et al., *Journal of Immunological Methods*, 130, 123–131 (1990).
Aron et al., *Journal of Clinical Microbiology*, vol. 31, No. 4, 975–978 (1993).
Laferriere et al., *Vaccine*, vol. 15, No. 2, 179–186 (1997).
Kristensen et al., *Apmis 100*, 142–146 (1992).
A. Esswein et al., *Helvetica Chimica Acta*, 72:213–223 (1989).
A. Esswein et al., *Carbohydrate Research*, 200:287–305 (1990).

*Primary Examiner*—Elli Peselev
(74) *Attorney, Agent, or Firm*—Peter F. Corless; Edwards & Angell, LLP

(57) ABSTRACT

The present invention provides a method for immobilizing a polysaccharide (PS) to a solid surface, said polysaccharide having a keto-carboxy group (—C(=O)—COOH) or a ketal or hemiketal group corresponding thereto, e.g. derived from KDO (2-keto-3-deoxy-D-manno-octonic acid)), the method comprising the steps of: (a) forming a covalent bond between the carboxy group of the polysaccharide and a reporter molecule (RM), thereby forming a polysaccharide-reporter molecule conjugate (PS-RM), said reporter molecule comprising a recognition/substrate site (e.g. biotin or an anthraquinone); and (b) immobilizing the polysaccharide-report molecule conjugate by forming a specific bond (e.g. by photocoupling or formation of an affinity pair) between the recognition/substrate site of said reporter molecule and a reception/reagent site of the solid surface. The present invention also provides a solid surface thus obtainable and the use of such solid surfaces for diagnostic purposes, e.g. for the detection of bacterial infections from Gram-negative bacteria that are human or veterinary pathogens, e.g. enterobacteria, respiratory bacteria, urogenitial bacteria, and neuropathogenic bacteria such as Salmonella sp., Actinobacillus sp.

22 Claims, 24 Drawing Sheets

METHOD FOR INTRODUCTION OF REPORTER GROUPS INTO BACTERIAL LIPOPOLYSACCHARIDE-DERIVED CARBOHYDRATES AND THE SUBSEQUENT COUPLING OF SUCH DERIVATIVES ONTO SOLID SURFACES

This application claims the benefit of U.S. Provisional Application No. 60/116,280, filed Jan. 19, 1999.

FIELD OF INVENTION

The present invention relates to a method for immobilising special classes of polysaccharides to solid surfaces. Such a method is highly valuable in the construction of reliable assays for the detection of an antibody corresponding to the polysaccharide antigen. The present invention also relates to modified solid surfaces and to the use of such surfaces in various diagnostic assays. Furthermore, the present invention relates to novel KDO derivatives which are valuable intermediates in the construction of such modified solid surfaces.

BACKGROUND OF INVENTION

Bacterial lipopolysaccharides (LPSs) are characteristic outer membrane constituents of Gram-negative bacteria. LPSs are widely used as antigens in diagnostic assays specially designed for the specific detection of antibodies in serum, plasma, meat juice, saliva or other body fluids, originating from bacterial infections in humans and animals. LPSs are highly immunogenic and comprise one of the epitope characteristics for a given bacterial strain. In fact, the definition of a serotype is often based on the LPS and/or capsular polysaccharide (CPS) antigenicity. The antigenic specificity of the LPS molecule resides in the polysaccharide part of the LPS, the O-antigen, whereas the toxicity of the LPS is caused by residues contained in the lipid part of the LPS, called the lipid A. LPSs are highly amphiphilic compounds because of the joint presence of a hydrophilic O-polysaccharide group and a hydrophobic lipid group in the LPS molecule. Most of the characterised LPSs have the same principal structure which is especially conserved in the lipid A and in the inner core parts of the LPSs. The core is the part of the polysaccharide that comprises the bond between the O-antigen and the lipid A. This bond is invariably comprised of a ketosidic bond between the hemiketal function of the innermost KDO-residue and a hydroxyl-group of a GlcNAc-residue of the lipid A. The O-antigen of a specific bacterial serotype varies with respect to numbers of repeating units and may contain non-stoicheometrical substitutions with acetyl, phosphate, glycosyl or other groups. Generally, LPS-molecules without O-antigens, that is carrying only (parts of) the core saccharides in addition to the lipid A are called "rough" LPS, while LPS-molecules carrying O-antigens are called "smooth" (Raetz, C. R. H. in *Escherichia coli* and Salmonella: Cellular and Molecular Biology (Neidhardt, F. C. E. A., ed.) Vol. 1, 2nd Ed., pp. 1035–1063, American Society for Microbiology, Washington D.C., 1996; Hitchcock et al, 1986, J. Bacteriol. 166, 699–705).

ELISA, enzyme-linked immunosorbent assay, is a well known method for detection of antibodies. In this assay, the LPSs are coated (or immobilised) on a solid surface (e.g. a plastic surface) by passive adsorption, where they serve as probes for specific antibodies. The method consists of incubation of the LPS-coated surface with the biological sample being assayed for the presence of antibodies, followed by incubation of the LPS-antibody complex with a labelled secondary antibody.

Previously, LPSs have generally been immobilised onto a solid surface without any modification of the molecules since the hydrophobic lipid A part of the molecules functions as a fairly efficient "anchor" binding the LPSs to the surface via non-covalent hydrophobic interactions leaving the hydrophilic O-polysaccharides pointing outward accessible for interactions with binding components, e.g. antibodies. However, it has been shown that the efficiency by which the LPSs are immobilised onto hydrophobic surfaces depends on both the nature of the surface and the equilibrium between free LPSs and formed LPS micelles. The equilibrium between free LPSs and formed LPS micelles depends on the amphiphilic nature of the LPSs and varies between LPSs from different bacteria strains as well as between different LPS serotypes. Certain types of LPSs have shown to be very difficult to immobilise onto solid surfaces by non-covalent bonds without addition of various micelle-dispersing agents (detergents) to the coating solution.

Thus, the optimal coating conditions vary among LPS from different bacteria strains as well as between serotypes of the same bacteria, making simultaneous immobilisation of two or more different LPSs onto the same surface very difficult. This is envisaged to be due to the ability of a well-coating LPS type to compete out the less well-coating type. This phenomenon was illustrated with *Salmonella Infantis* LPS which was shown to coat inefficiently to plastic. In an assay for detection of *Salmonella Typhimurium* and *Salmonella Infantis* specific antibodies this lead to the substitution of *Salmonella Infantis* LPS with *Salmonella Choleraesuis* LPS which was found to coat much better and which carries the same antigenic serotypes (O-antigens) (Neilsen, B. et al., 1995, Vet. Microbiol. 47, 205–218)

The tendency of LPS to form micelles (or aggregates) is furthermore believed to reduce the stability of the LPS coating as the interactions between bimolecular (or aggregated or cluster) LPS and the surface are believed to be weaker then the interactions between a single molecule of LPS and the surface. In other words, the potential tendency of LPS to coat in clusters may lead to a decreased and unpredictable coating stability and reduce the long-term stability of the coating.

EP 0 101 119 describes the immobilisation of a lipopolysaccharide to an insoluble carrier by the condensation of the lipopolysaccharide and either an amino or carboxyl group of the insoluble carrier.

JP-A-2-242448 (Patent Abstract of Japan) describes the immobilisation of a lipid A glycoside of 3-deoxy-D-manno-2-octurosonic acid to the surface of an insoluble carrier through an amide bond.

Highly hydrophilic antigens like e.g. bacterial polysaccharide (PS) are often very difficult to adsorb (immobilise) onto the most commonly used surfaces used in serological assays, such as plastics used in ELISA and RIA (radio-immuno assay), latex particles used in agglutination techniques and PVDF (polyvinylidenedifluoride) as well as nitrocellulose and other materials used for dip-stick, blotting or other fast assays. Accordingly, PS as such coat inefficiently and demand the use of large quantities of polysaccharide antigen or extremes of pH and can not be used with mixtures of polysaccharides (Elkins et al., 1990, J. Immunol. Meth. 130, 123–131). On the contrary, in spite of the drawbacks mentioned above LPSs are almost exclusively used as coating antigens as the lipid A provides the required hydrophobicity needed for adequate coating of the surface with antigen.

PSs have previously been isolated from LPSs with the purpose of preparing conjugates of PS and carrier substances, most often carrier proteins for vaccine purposes (Aron et al., 1993, J. Clin. Microbiol. 31, 975–978; Lambden and Heckels, 1982, J. Immunol. Meth. 48, 233–240; Gupta et al., 1995, Inf. Immun. 63, 2805–2810).

Previously, it has been shown that the polysaccharide part of *Salmonella Typhimurium* lipopolysaccharide (LPS) could be derivatised with biotin and immobilised onto a streptavidin-coated ELISA-plate where it could be recognised by antibodies against PS. By using the hydrazide derivative of biotin, it was possible to react the PS directly with biotin-hydrazide without a prior oxidation step; the hydrazide was shown to react with the hemiketal of the reducing end KDO of the PS. This procedure while leading to antigenically intact biotinylated PS-derivatives, however resulted in derivatives that were not stable, and an avidin or streptavidin coating had to be introduced in the assay (Wiuff, C., Lind, P., Heegaard, P., 1997, Regioselective coupling of reducing carbohydrates to hydrazides for derivatization of bacterial polysaccharides and application to immunoassays, Proc. $2^{nd}$. Carbohydrate Engineering Meeting, La Rochelle, France, p. 66).

In Meikle et al. (Glycoconjugate J. 7, 207–218, 1990) a PS is used in an ELISA by directly coupling the PS to a detection enzyme in a competitive set-up. The coupling was performed by reductive amination of the keto functionality of the keto-carboxy group of a KDO unit of the PS. The PS/detection enzyme conjugate was not used for coating but was used in solution in a later step in the assay.

Generally, binding of PS to solid surfaces requires modifications of the PS molecule, but in such a way the O-antigen part stays unaltered. A number of such modifications have been described for naturally occurring polysaccharides. A well-known example is the coupling of capsular polysaccharides (CPSs), which do not contain hydrophobic parts (or groups), to proteins (Laferrière et al., 1997, Vaccine 15, 179–186; Beuvery et al., 1986, Develop. biol. Standard. 63, 117–128.). The resulting capsular polysaccharide-protein complexes are then adsorbed to the surfaces through hydrophobic groups in the carrier protein. Bacterial capsular polysaccharides have also been modified by non-regioselective reaction of hydroxyl groups with hydrophobic groups e.g. phenyl or thyramine to enhance the overall hydrophobicity of the CPS molecules and there by the binding abilities to solid surfaces (Kristensen and Bentzon, 1992, APMIS 100, 142–146).

A major problem is that antigenicity may be difficult to retain after derivatisation of the polysaccharide, as most methods are not directed to the derivatisation of any specific region of the polysaccharide antigen, thereby possibly destroying or modifying antigenic epitopes of the polysaccharide.

This has been overcome with the present invention by restricting the derivatisation to certain regions of the carbohydrate.

BRIEF DESCRIPTION OF THE INVENTION

Figure 1:
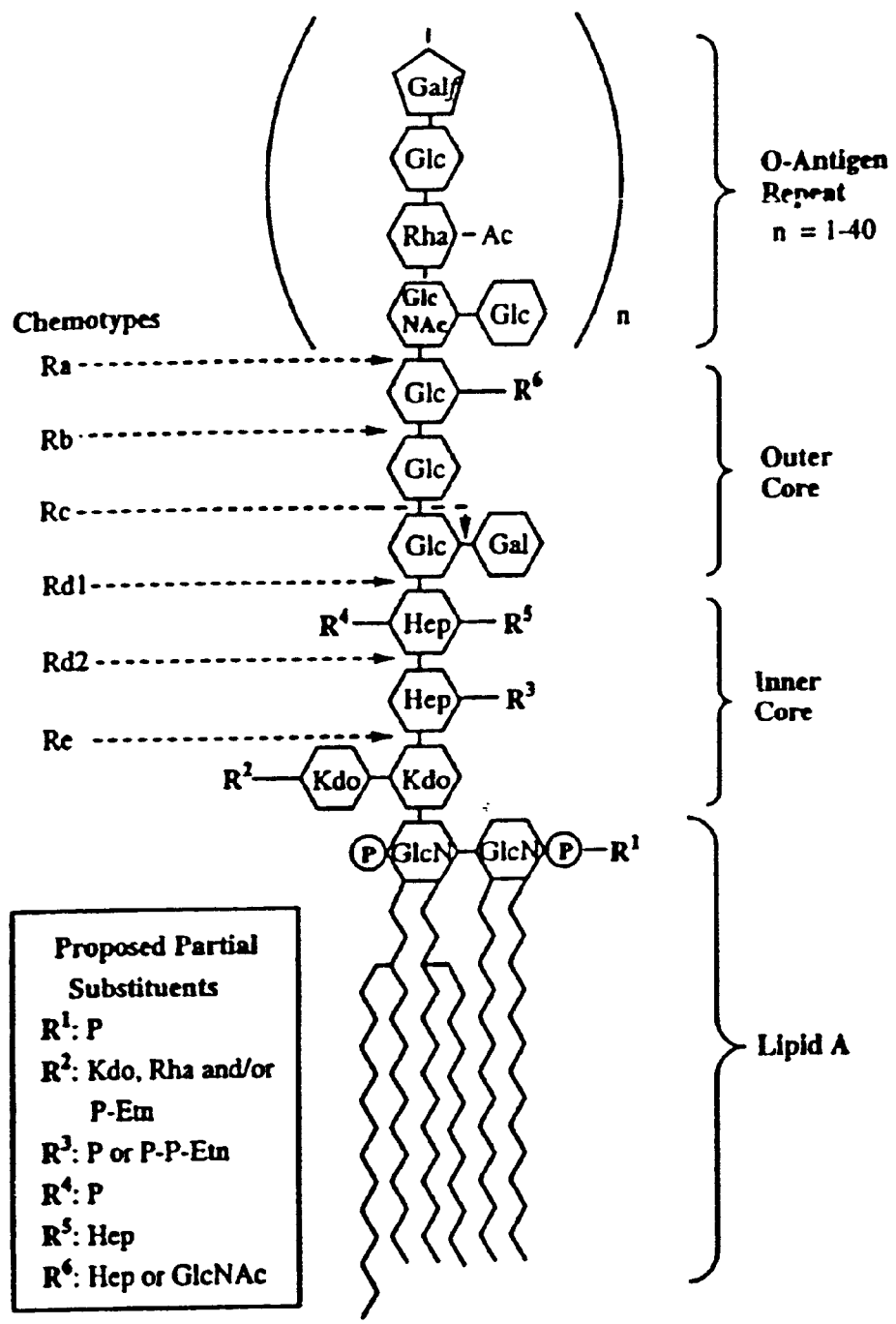
FIG. 1: Schematic molecular structure of *E. Coli* K12 LPS. Abbreviations: GlcN, D-glucosamine; Kdo, 3-deoxy-D-manno-octulosonic acid; Hep, L-glycero-D-manno-heptose; Glc, D-glucose; Gal, D-galactose; GlcNAc, N-acetyl-D-glucosamine; Rha, L-rhamnose; Galf, D-galactofuranose; P, phosphate; P-Etn, phosphoethanolamine; P-P-Etn, ethanolamine pyrophosphate; Ac, acetate.

The present invention provides novel methods for immobilising a polysaccharide to a solid surface.

Thus, the present invention provides a method for immobilising a polysaccharide (PS) to a solid surface, said polysaccharide having a keto-carboxy group (—C(=O)—COOH) or a ketal or hemiketal group corresponding thereto), the method comprising the steps of:
a) forming a covalent bond between the carboxy group of the polysaccharide and a reporter molecule (RM), thereby forming a polysaccharide-reporter molecule conjugate (PS-RM), said reporter molecule comprising a recognition/substrate site; and
b) immobilising the polysaccharide-report molecule conjugate (PS-RM) by forming a specific bond between the recognition/substrate site of said reporter molecule and a reception/reagent site of the solid surface.

The present invention also provides a solid surface thus obtainable and the use of such solid surfaces for diagnostic purposes.

Furthermore, the present invention provides a compound of the general formula I

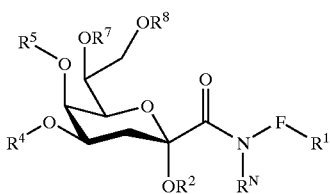

(or, in the case where $R^2$ is hydrogen, optionally the keto analogue thereof) wherein
$R^1$ is selected from hydrogen and a reporter molecule L-R, where L is an optional linker part of the reporter molecule, and R is a report part of the reporter molecule;

$R^N$ is selected from hydrogen and $C_{1-4}$-alkyl;
F is selected from a single bond, phenylene, carbonyl (C(=O)), carbonylimino (C(=O)—NH—), thiocarbonyl ((C(=S)) and imino (—NH—);
$R^2, R^7, R^8$ are each independently selected from hydrogen and hydroxy protecting groups;
$R^4$ is selected from hydrogen, a mono- or disaccharide residue and a hydroxy protecting group; and
$R^5$ is selected from hydrogen, an "optionally functional group protected polysaccharide residue" and a hydroxy protecting group,
and a method for preparation thereof.

It is, thus, a special object of the present invention to provide a method for the regioselective coupling of LPS derived bacterial polysaccharides to solid surfaces, said method being generic for all types of such LPS derived bacterial polysaccharides, said method further having no influence on the antigenic structure of the polysaccharide and finally, not introducing components adding to the non-specific background or undesired cross-reactivity when the immobilised polysaccharide is used in an assay.

DETAILED DESCRIPTION OF THE INVENTION

As mentioned above, the present invention, i.a., relates to a method for immobilising a polysaccharide (PS) to a solid surface.

In the present context, the term "polysaccharide" is intended to mean an entity comprising two or more glycoside linked monosaccharide units. Preferably the "polysaccharide" comprises at least 5, e.g. 5–1000, linked monosaccharide units, such as at least 10, e.g. 10–1000, linked monosaccharide units, in particular at least 25. e.g. 25–500, linked monosaccharide units. The polysaccharide may be linked so as to form a linear or branched polysaccharide.

The individual monosaccharides are typically naturally-occurring monosaccharides known to the person skilled in the art as constituents in polysaccharides of natural origin. Examples of such monosaccharides are ribose, deoxyribose, arabinose, xylose, apiose, fucose, rhamnose, fructose, glucose, mannose, galactose, glucosamine, muramic acid, galactosamine, glucoronic acid, iduronic acid, mannuronic acid, guluronic acid, galactoronic acid, glycero-manno-heptose, 3-deoxy-manno-octulosonic acid, neuraminic acid (5-amino-3,5-dideoxy-D-glycero-D-galacto-nonulosonic acid), abequose, N-acetyl-galactosamine, and N-acetyl-galactofuranose. Particularly interesting examples are D-ribose, D-deoxyribose, D-arabinose, D-xylose, D-apiose, L-fucose, L-rhamnose, D-fructose, D-glycose, D-mannose, D-galactose, L-galactose, D-glucosamine, muramic acid, D-galactosamine, D-glucoronic acid, L-iduronic acid, D-mannuronic acid, L-guluronic acid, D-galactoronic acid, L-glycero-D-manno-heptose, 3-deoxy-D-manno-octulosonic acid (KDO), neuraminic acid (5-amino-3,5-dideoxy-D-glycero-D-galacto-nonulosonic acid), abequose, N-acetyl-D-galactosamine, and N-acetyl-D-galactofuranose. Most interesting are D-glucosamine, KDO, L-glycero-D-manno-heptose, D-glucose, D-galactose, N-acetyl-D-glucosamine, L-rhamnose, and D-galactofuranose.

The polysaccharide may be essentially unsubstituted but due to the typical biological origin of the polysaccharide, it is typically non-stoichiometrically substituted with acetyl, phosphate, pyrophoshate, phosphoethanolamine, ethanolamine pyrophosphate, O-methyl, sulphate, or other groups.

The molecular weight of the polysaccharide (including any substituents) is preferably at least 1,000, e.g. in the range of 1,000–200,000, in particular at least 2,000, e.g. in the range of 2,000–200,000, especially at least 5,000.

Naturally-occurring bacterial lipopolysaccharides are normally present as a mixture of molecules differing in the number of repeating units and, consequently in molecular weight as has been repeatedly shown with lipopolysaccharides in some bacterial strains consisting of molecules with none to 40 repeating units, covering molecular weights from below 10 to above 100 kD (Goldman and Leive, 1980, Eur. J. Biochem. 107, 145–153). (A repeating unit is the monosaccharide or more commonly the oligosaccharide being repeated in the O-polysaccharide (see e.g. FIG. 1). Examples of such interesting oligosaccharide repeating units include the tetrasaccahride repeating unit of *Salmonella Typhimurium* and the acetylated pentasaccharide unit of *Escherichia coli* K12 (Raetz 1996).) Commonly, molecular weights of LPS derived polysaccharides may lay in the range of 2 to 50 kD, corresponding to 0 to 40 repeating units, often with a bimodal distribution with an overrepresentation of molecules with zero and one repeating unit and of molecules with 25–35 repeating units, respectively (Raetz 1996). It is often advantageous to retain the molecular weight distribution of the natural LPS in order to reflect the exact antigenicity of the intact O-antigens.

Thus, it should be understood that the above-stated ranges for numbers of monosaccharide units and molecular weights relate to the average number of monosaccharides found in the naturally occurring LPSs.

The polysaccharide which is to be immobilised comprises a keto-carboxy group (—C(=O)—COOH) or a ketal or hemiketal group corresponding thereto) which is a crucial anchor point for establishment of the link to the solid surface. In many instances (and preferably), this keto-carboxy group is provided by a KDO (2-keto-3-deoxy-D-manno-octonic acid) monosaccharide unit included in the polysaccharide. One or more KDOs are present in the inner core oligosaccharide of all known Gram-negative lipopolysaccharides as one or more (typically 3; see FIG. 1) linked monosaccharides. One of these KDOs comprises the glycosidic bond to the hexosamine dimer of the lipid A and one, being the same KDO monosaccharide or another KDO monosaccharide comprises the glycosidic bond to the reducing end of the rest of the polysaccharide part of the lipopolysaccharide.

FIG. 1 illustrates a typical Gram-negative bacterial lipopolysaccharide from *E. coli* K-12 (from Raetz 1996).

The polysaccharides for which the present invention is especially applicable are polysaccharides which are substantially identical to the carbohydrate part of a Gram-negative bacterial lipopolysaccharide (LPS). By the "carbohydrate part of a Gram-negative bacterial lipopolysaccharide" is meant the entire polysaccharide chain, or "tree" of the lipopolysaccharide except the monosaccharides derivatised with fatty acids in ester- and/or amide bonds comprising the lipid A part. Furthermore, the carbohydrate part does not necessarily comprise all KDO units of the entire polysaccharide chain (see below).

Figure 2:
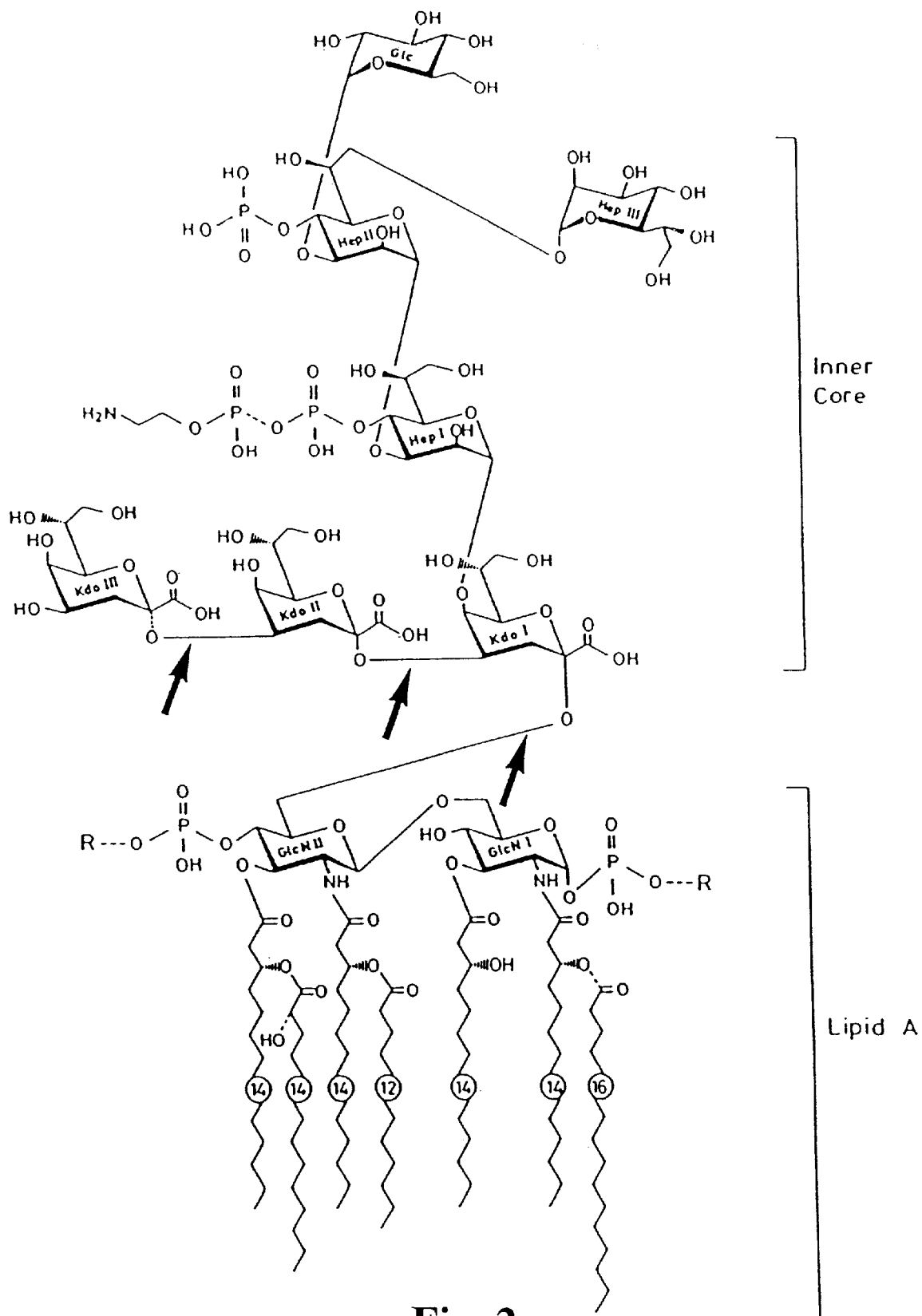
FIG. 2: Shows the inner core and lipid A part of LPS from a typical Gram-negative bacteria.

By "substantially identical" is preferably also meant that the polysaccharide has substantially the same biological binding activity as the carbohydrate part of the native lipopolysaccharide. This means that the outer core part and the O-antigen (the serotype specific part) of the polysaccharide is preferably substantially identical to that of the native bacterial lipopolysaccharide, whereas some inner core monosaccharide (e.g. one or two, but not all, KDO units) may have been chemically cleaved off when the carbohydrate part is chemically cleaved from the lipid A part (see FIG. 2 for the possible points of attack of a lipopolysaccharide (LPS) leading to a polysaccharide (PS)). It is important to note that the feature of the polysaccharide is that the serotype specificity is substantially preserved, i.e., that the O-antigen portion of the native lipopolysaccharide (LPS) is substantially unaffected by the cleavage.

The inner core of a lipopolysaccharide polysaccharide is defined as the well-conserved KDO and heptose-containing reducing oligosaccharide of Gram-negative bacterial lipopolysaccharide, said oligosaccharide containing the linkage between KDO and lipid A.

Lipid A is the well-conserved part of bacterial lipopolysaccharides comprising fatty acids bound to a substituted hexosamine dimer, which, in turn, is the unit bound to the reducing KDO of the inner core in unmodified lipopolysaccharide.

Preferably, the polysaccharide is obtained (or at least obtainable) by the selective hydrolysis of the ketal bond between the inner core part and the lipid A part of a Gram-negative bacterial lipopolysaccharide. Preferably substituents on the polysaccharide like acetyl, phosphate, pyrophoshate, phosphoethanolamine, ethanolamine pyrophosphate, O-methyl, sulphate, or other groups are not cleaved during the selective hydrolysis.

"Selective hydrolysis" means a chemically or enzymatically mediated hydrolysis preferentially cleaving a selected glycoside bond, i.e. in the present context, the bond between the lipid A part and the KDO part.

Although the present invention is applicable (and advantageous) for polysaccharides (PS—i.e. polysaccharides without a lipid part) derived from Gram-negative bacterial lipopolysaccharides (LPS), it should be understood that it is believed realistic and possible to use the complete lipopolysaccharide (LPS) of Gram-negative bacteria in the method according to the invention with a fair result. This is believed to be possible due to the fact that the lipopolysaccharide as such comprises the necessary keto-carboxy group. This constitutes a separate embodiment of the present invention. Thus, the present invention also provides a method, wherein the polysaccharide further comprises the lipid part of a Gram-negative bacterial lipopolysaccharide, i.e. the "polysaccharide" thereby constituting a bacterial lipopolysaccharide.

The bacteria from which the polysaccharides (and thereby also the lipopolysaccharides) are derived are preferably Gram-negative bacteria that are human or veterinary pathogens such as enterobacteria, respiratory bacteria, urogenitial bacteria, and neuropathogenic bacteria.

Examples of bacteria which give rise to especially applicable polysaccharides within the present invention are selected from human Gram-negative bacteria comprising *Haemophilus* sp, *Echerichia coli* ssp, *Salmonella* sp, *Klebsiella* sp, *Bordetella* sp, *Pseudomonas* sp, *Chlamydia* sp, *Neisseria* sp, *Vibrio cholerae*, *Shigella* sp, *Proteus* sp, *Brucella* sp, *Streptobacillus* sp, *Yersinia* sp, *Legionella pneumophila*, and *Serratia marcescens*, especially *Haemophilus influenzae*, *Salmonella enterica* ssp., *Klebsiella pneumoniae*, *Bordetella pertussis*, *Psdueomonas aeruginosa*, *Chlamydia psitacci*, *Neisseria meningitidis*, *Neisseria gonorrhea*, *Vibrio cholerae*, *Shigella flexneri*, and *Shigella dysenteriae*, and veterinary or zoonotic bacteria including enterobacteria selected from *Escherichia coli*, *Salmonella Typhimurium*, *Salmonella Choleraesuis*, *Salmonella enterica*, and all serotypes hereof, especially *Salmonella Typhimurium*, *Salmonella Enteritidis*, *Salmonella*

*Choleraesuis, Salmonella Manhattan, Salmonella Dublin, Salmonella Infantis, Escherichia coli* spp. including O157, oedema-disease causing *Escherichia coli, Yersinia enterocolitica,* and *Campylobacter jejuni,* as well as respiratory bacteria selected from the HAP group of bacteria especially Actinobacillus sp, in particular the HAP group bacteria *Actinobacillus pleuropneumoniae, Haemophilus somnus, Pasteurella haemolytica, Pasteurella multocida, Haemophilus parasuis* and Mannheimia sp.

Isolation of LPS

LPSs are generally isolated from Gram-negative bacteria by aqueous phenol extraction followed by various purification steps (Raetz 1996). These methods can in general be applied to all types of bacterial LPS. Also, LPSs are commercially available.

Characterisation of LPS

Isolated LPS can be characterised by a number of different methods as described in the Experimental section. SDS-PAGE (sodium dodecyl sulfate polyacrylamide gel electrophoresis) can be used to analyse the molecular weight distribution of the LPS. Both smooth and rough LPSs including commercially available materials can be analysed by this method. Also mass spectrometry, NMR, indirect ELISA (see the Experimental section), UV-spectrometry (see the Experimental section), immuno-blotting and other methods can be used.

Preparation of PS

It is well-known that the intact O-antigen can be isolated from the LPS by cleavage of the O-polysaccharide from the lipid A part. This is routinely done by acidic hydrolysis (e.g. 0.1 M acetic acid at 90° C. for 1 hour) of the acid-labile glycoside bond between the reducing ends of the KDO in the O-polysaccharide, and the GlcNAc in the lipid A-part of LPS, followed by aqueous chloroform/methanol extraction to afford the polysaccharide (PS) (Raetz 1996).

The isolated PS contains the (substantially) intact O-antigen of the LPS. Elimination of the lipid A from the PS facilitates the accessibility of antibodies to the O-antigen (Munford and Hall, 1979, Inf. Imm. 26, 42–48) as well as decrease the endotoxicity of the O-antigen about 1000 times relatively to the corresponding LPS (van de Wiel et al., 1987, Vaccine 5, 33–38). In addition, PSs are pure hydrophilic molecules, they are of low toxicity, highly soluble in aqueous solutions and show no tendency to form micelles. PSs are therefore easier to handle than LPSs.

Other methods that may be used to obtain delipidated LPS polysaccharides include alkaline hydrolysis by hydrazine or NaOH, releasing esterified fatty acids in addition to phosphate and other esters, but not amide-bound fatty acids (Gupta et al. 1995) and phage-mediated degradation of the O-polysaccharide of intact LPS or PS into smaller oligosaccharide units, not retaining the terminal KDO monosaccharide (Svenson et al. 1979, J. Virol. 32, 583–592). In addition to the phase-extraction method employed in the examples it is well-known that PS can be worked up from acid hydrolysis by gel permeation chromatography (Lambden and Heckels, 1982).

Characterisation of PS

Isolated PS can be characterised by a number of different methods as described in the Experimental section. SDS-PAGE (sodium dodecyl sulfate polyacrylamide gel electrophoresis) can be used to analyse for remaining LPS. Also mass spectrometry, NMR, indirect and competitive ELISA (see the Experimental section), UV-spectrometry (see the Experimental section), immuno-blotting and other methods can be used.

Preparation of polysaccharide reporter group conjugates

To obtain the best performance of an immobilised polysaccharide antigen in a diagnostic assay or other applications, it is necessary to immobilise the antigen in a well defined orientation on the solid surface. Within the present invention, this requires the regiospecific formation of a chemically stable bond between a reporter molecule and the polysaccharide antigen.

As mentioned above, the method of the present invention includes the step of forming a covalent bond between the carboxy group of the polysaccharide (PS) and a reporter molecule (RM), thereby forming a polysaccharide-reporter molecule conjugate (PS-RM), wherein said reporter molecule comprises a recognition/substrate site.

The term "reporter molecule" is intended to mean a chemical entity which is used to establish the specific link between the polysaccharide and the solid surface. The reporter molecule comprises at least a reporter part which includes the recognition/substrate site, and optionally a linker part.

The polysaccharide-reporter molecule conjugate (PS-RM) preferably has the general formula PS'—C(=O)—N($R^N$)—F—L—R, where PS'—C(=O) is the polysaccharide, N($R^N$)—F is the group directly involved in the covalent link between the polysaccharide and the reporter molecule, $R^N$ designates hydrogen or $C_{1-4}$-alkyl, L is the linker part of the reporter molecule, and R is the reporter part of the reporter molecule. In particular, —N—F— designates amino (—N—), anilino (—N—Ph), hydrazido (—N—C(=O)—), semicarbazido (—N—C(=)—NH—), thiosemicarbazido (—N—C(=S)—NH—), or hydrazino (—N—NH—). Preferably —N—F— is amino.

The term "$C_{1-4}$-alkyl" is intended to cover methyl, ethyl, propyl (1-propyl and 2-propyl), cyclopropyl, butyl (1-butyl, 2-butyl, 2-methyl-prop-1-yl and 2-methyl-prop-2-yl (tert-butyl)).

Various types of reporter parts are generally described below under "Immobilisation of polysaccharide reporter molecule conjugates".

Examples of reporter parts are photochemically reactive groups such as substituted coumarins, benzofurans, indols, angelicins, psoralens, carbene and nitrene precursers, ketones, and quinones, e.g. anthraquinones (AQ), phenanthraquinones and benzoquinones; thermochemically reactive groups such as carboxylic acids, primary amines, secondary amines, acid hydrazides, semicarbazides, thiosemicarbazides, thiols, aliphatic hydrazines, aromatic hydrazines, epoxides and maleimides; and one part of an affinity pair (preferably the part having the lower molecular weight, e.g. a molecular weight of up to 7,000) such as one part of biotin/avidin, biotin/streptavidin, biotin/NeutrAvidin™, glutathione/glutathione-S-transferase, iminodiacetic acid metal complex/hexa-histidine tagged peptides and proteins, nitrilotriacetic acid metal complex/hexa-histidine tagged peptides and proteins, LNA/LNA, LNA/DNA, LNA/RNA, DNA/DNA, DNA/RNA, RNA/RNA, PNA/RNA, PNA/DNA and mono- or polyclonal antibodies raised against a specific hapten/hapten. Preferably, the reporter part comprises a biotin (a part of an affinity pair) or an anthraquinone.

The reporter molecule may also include a suitable linker part (L) in addition to a reporter part. Such linker may be useful in providing a sufficient flexibility/mobility of the immobilised polysaccharide.

The optional linker part between the reporter molecule and the polysaccharide can be used for different purposes. The linker part may be used to space the reporter group from the polysaccharide thus, enhancing the subsequent immobilisation step. At the same time the spacer also enhances the presentation of the polysaccharide epitopes improving an diagnostic assay or other applications based on the immobilised polysaccharide. Appropriate linkers may also provide charged, uncharged, hydrophilic or hydrophobic moieties as desired influencing e.g. the solubility of the reporter group spacer molecule during conjugation to the polysaccharide as well as the properties of the final application of the immobilised polysaccharide. Thus, appropriate conjugate design and optimised conjugation protocols are key elements in the ability to produce optimal polysaccharide reporter group conjugates for the subsequent immobilisation to solid surfaces.

Examples of linker parts are biradicals selected from $C_{1-20}$-alkylene optionally comprising aromatic or mono-/polyunsaturated hydrocarbons or cyclic hydrocarbons, oligo-oxyethylenes, oligo-amides such as oligo-glycine, oligo-alanine, oligo-lysine and oligopeptides in general, oligo-phospodiesters, oligo-phosphoamidates, oligo-phosphodiamides, oligo-sulfonesters, and oligo-sulfonamides. Moreover, the linker may also consist of combined units of the aforementioned.

It is preferred that the linker part, if present, introduces 1–30 atoms, preferably 3–20 atoms, between the F and R in the above formula PS'—C(=O)—N($R^N$)—F—L—R (and in the above formula I)

Preferably, the reporter molecule has a molecular weight of at the most 10,000, such as at the most 5,000, preferably at the most 2,500.

The term "recognition/substrate site" of the reporter part of a reporter molecule is intended to mean the site being, or including, a (biologically) recognition site (i.e. one part of an affinity pair) or a chemically reactive part of a photochemically reactive part which is intended to form a specific bond with a reception/reagent site of the solid surface.

As mentioned above, it has been found that the carboxylic acid in a keto-carboxy containing monosaccharide unit in a polysaccharide is a especially good handle for regiospecific as well as chemoselective bond formation between the polysaccharide and a reporter molecule containing a suitable functional group.

Several nucleophiles including primary and secondary amines, aliphatic hydrazines, aromatic hydrazines, semicarbazides, thiosemicarbazides and acid hydrazides are able to form a stable covalent bond with a carboxylic acid moiety with the aid of a coupling reagent. Thus, reporter groups containing such nucleophilic groups will be able to form stable covalent bonds with a carboxylic acid. It should be understood that some "reporter parts" may in themselves comprise such a nucleophile. Alternatively such a nucleophile may be introduced directly or via the optional linker part (L). Preparation of such nucleophile containing reporter molecules is well-known to the person skilled in the art (see e.g. Greg T. Hermanson et. al., Immobilized Affinity Ligand Techniques, Academic Press Inc., 1992).

The coupling reagent acts as an activator of the carboxylic acid and a subsequent attack by the nucleophile leads to the formation of a stable covalent bond. Examples of coupling reagent are carbodiimides such as diisopropyl carbodiimide and water soluble carbodiimide (WSC, 1-(3-dimethylaminopropyl)-3-ethyl carbodiimide), phosphonium salts such as benzotriazolyloxy-tris-(dimethylamino) phosphonium hexafluorophosphate (BOP) and (benzotriazolyl)-N-oxy-pyrrolidinium phosphonium hexafluorophosphate (PyBOP), uronium salts such as O-benzotriazolyl-N,N,N',N'-tetramethyluronium hexafluorophosphate (HBTU), O-(3,4-dihydro-4-oxo-1,2,3-benzotriazinyl)N,N,N',N'-tetramethyluronium tetrafluoroborate (TBTU), and N,N'-Tetramethyl fluoroformimidinium hexafluorophosphate (TFFH). Many other coupling reagents may be used and are known to the person skilled in the art (M. Bodanszky, Principles of Peptide Synthesis, 2nd Edition, Springer-Verlag, 1993). The addition of helper nucleophiles such as N-hydroxy succinimide and 1-hydroxy benzotriazole may enhance the coupling kinetics as well as suppressing side reactions such as O→N acyl rearrangements when using carbodiimides as coupling reagents (M. Bodanszky, Priciples of Peptide Synthesis, 2nd Edition, Springer-Verlag, 1993).

The coupling reactions can be performed in aqueous solution or in a mixture of water and an water miscible organic solvent such as N,N-dimethyl formamide, dimethyl sulfoxide, dioxane, methanol, ethanol and acetone or in the pure organic solvent. The solvent or solvent mixture is selected to allow the best possible solubility of the reactants.

When using water or a water organic solvent mixture the pH during the coupling reaction can be controlled by using a buffer solution. The pH is selected to allow the best conditions for the coupling reaction while at the same time preserving the integrity of the polysaccharide and reporter molecule. Preferentially the pH is kept between 5 and 9 in order to preserve acid or base labile epitopes on the O-chains of the polysaccharide. An example of such a labile group is O-acetyl functionalities which are very commonly found in polysaccharide O-antigens. The optimum pH for the coupling reaction also depends on the nature of the nucleophile. Amines are basic compounds that are protonised at low pH which renders them non-nucleophilic and thus, coupling reactions using amines are best performed at a pH above 7. Other nucleophiles such as aromatic hydrazines, semicarbazides, thiosemicarbazides and acid hydrazides are much less basic allowing the coupling reaction to be performed at neutral pH or even lower. Another factor which determines the optimum pH for the coupling reaction is the competing hydrolysis of the activated carboxylic acid moiety by the attach of hydroxide ions. This side reaction can be minimised by the use of a pH below 8 during coupling. In organic solvents the pH during the coupling reaction can be achieved by the use of suitable organic or inorganic acids and bases that are selected according to their solubility in the solvent as well as according to their relative acid or base strength. As described above, the precise conditions are chosen as promote the covalent coupling while at the same time preserving the integrity of the polysaccharide and reporter molecule.

The coupling reactions are typically performed at a temperature in the range of –20–100° C., often 0–20° C. such as around 5° C.

In addition to the above mentioned parameters reaction time as well as the amount of polysaccharide, coupling reagent and reporter group are critical for obtaining the ideal polysaccharide reporter group conjugate. The inventors have developed coupling protocols which yield reproducible conjugates in excellent yields and quality preserving the immunogenic epitopes of the polysaccharide as well as the integrity of the reporter group (see the Experimental section). Such optimisation is often desirable for commercial applications as will be apparent for the person skilled in the art.

In an interesting and commercially very interesting embodiment of the present invention, the polysaccharide is a polysaccharide derived from Salmonella LPS, and the reporter molecule which is coupled to the polysaccharide via an amide bond by means of a carbodiimide coupling reagent comprises a biotin or anthraquinone group.

Another an interesting and commercially very interesting embodiment of the present invention, the polysaccharide is a polysaccharide derived from Actinobacillus LPS, and the reporter molecule which is coupled to the polysaccharide via an amide bond by means of a carbodiimide coupling reagent comprises a biotin or anthraquinone group.

These embodiments are thoroughly discussed in the Experimental section.

It is believed that the intermediates produced according the first step of the method according to the present invention are novel as such.

Thus, the present invention also provides a compound of the general formula I

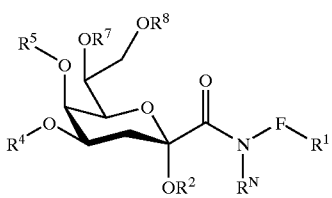

(or, in the case where $R^2$ is hydrogen, optionally the keto analogue thereof) wherein $R^1$ is selected from hydrogen and a reporter molecule L-R, where L is an optional linker part of the reporter molecule, and R is a report part of the reporter molecule;

$R^N$ is selected from hydrogen and $C_{1-4}$-alkyl;

F is selected from a single bond, phenylene, carbonyl (C(=O)), carbonylimino (C(=O)—NH—), thiocarbonyl ((C(=S)) and imino (—NH—);

$R^2, R^7, R^8$ are each independently selected from hydrogen and hydroxy protecting groups;

$R^4$ is selected from hydrogen, a mono- or disaccharide residue and a hydroxy protecting group; and $R^5$ is selected from hydrogen, an "optionally functional group protected polysaccharide residue" and a hydroxy protecting group.

The term "mono- or disaccharide residue" is intended to mean a residue comprising one or two glycosidically linked monosaccharide units. Preferred examples are KDO-2-yl, 4-phosphoethanolamine-KDO-2-yl, L-rhamnosyl-(1→4)-KDO-2-yl, and KDO-(2→4)-KDO-2-yl.

The term "polysaccharide residue" is intended to mean the part of a polysaccharide (as defined above) which together with the KDO monosaccharide unit of formula I and any $R^4$ saccharide substituents forms the polysaccharide (PS). Thus, the polysaccharide residue preferably comprises from 2–997 linked monosaccharide units, such as at least 7, e.g. 7–997, linked monosaccharide units, in particular at least 22, e.g. 22–497, linked monosaccharide units. As defined above for "polysaccharide", the polysaccharide residue may be non-stoichiometrically substituted.

The term "optionally functional group protected" is intended to mean that the oligosaccharide fragment which carries functional groups which are reactive under the conditions prevailing in coupling steps, are optionally functional group protected as known in the art. This means that groups such as hydroxy, amino, carboxy, sulphono, and mercapto groups are optionally functional group protected. Protection (and deprotection) is performed by methods known to the person skilled in the art (see, e.g., Greene, T. W. and Wuts, P. G. M., "Protective Groups in Organic Synthesis" $2^{nd}$ ed., John Wiley, N.Y. (1991), and M. J. Gait, Oligonucleotide Synthesis, IRL Press, 1984).

Illustrative examples of "hydroxy protection groups" are optionally substituted trityl, such as 4,4'-dimethoxytrityl (DMT), 4-monomethoxytrityl (MMT), and trityl, optionally substituted 9-(9-phenyl)xanthenyl(pixyl), optionally substituted ethoxycarbonyloxy, p-phenylazophenyloxycarbonyloxy, tetraahydropyranyl (thp), 9-fluorenylmethoxycarbonyl (Fmoc), methoxytetrahydropyranyl (mthp), silyloxy such as trimethylsilyl (TMS), triisopropylsilyl (TIPS), tert-butyldimethylsilyl (TBDMS), triethylsilyl, and phenyldimethylsilyl, benzyloxycarbonyl or substituted benzyloxycarbonyl ethers such as 2-bromo benzyloxycarbonyl, tert-butylethers, alkyl ethers such as methyl ether, acetals (including two hydroxy groups), acyloxy such as acetyl or halogen substituted acetyls, e.g. chloroacetyl or fluoroacetyl, isobutyryl, pivaloyl, benzoyl and substituted benzoyls, methoxymethyl (MOM), benzyl ethers or substituted benzyl ethers such as 2,6-dichlorobenzyl(2,6-$Cl_2Bzl$). Alternatively, a hydroxy group may be protected by attachment to a solid support optionally through a linker.

Illustrative examples of amino protection groups are Fmoc (fluorenylmethoxycarbonyl), BOC (tert-butyloxycarbonyl), trifluoroacetyl, allyloxycarbonyl (alloc, AOC), benzyloxycarbonyl (Z, Cbz), substituted benzyloxycarbonyls such as 2-chloro benzyloxycarbonyl ((2-ClZ), monomethoxytrityl (MMT), dimethoxytrityl (DMT), phthaloyl, and 9-(9-phenyl)xanthenyl(pixyl).

Illustrative examples of carboxy protection groups are allyl esters, methyl esters, ethyl esters, 2-cyanoethylesters, trimethylsilylethylesters, benzyl esters (Obzl), 2-adamantyl esters (O-2-Ada), cyclohexyl esters (OcHex), 1,3-oxazolines, oxazoles, 1,3-oxazolidines, amides and hydrazides.

Illustrative examples of mercapto protecting groups are trityl (Trt), acetamidomethyl (acm), trimethylacetamidomethyl (Tacm), 2,4,6-trimethoxybenzyl (Tmob), tert-butylsulfenyl (StBu), 9-fluorenylmethyl (Fm), 3-nitro-2-pyridinesulfenyl (Npys), and 4-methylbenzyl (Meb).

In an interesting embodiment, $R^1$ is L-R. Furthermore, —N—F— in the formula I preferably designates amino (—N—), anilino (—N—Ph), hydrazido (—N—C(=O)—), semicarbazido (—N—C(=O)—NH—), thiosemicarbazido (—N—C(=S)—NH—) or hydrazino (—N—NH—), in particular amino.

The group L preferably designates a biradical (linker part) as defined above and, furthermore, the reporter molecule (L-R) is preferably also as defined above. Variants where the reporter molecule comprises a biotin or an anthraquinone (in particular an anthraquinone) as a part of the reporter part are especially interesting.

Furthermore, the present invention provides a method for the preparation of a compound of the general formula I as defined above, comprising reacting a compound of the general formula III

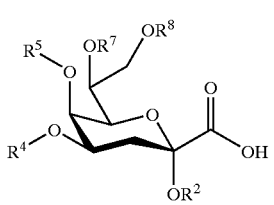

wherein $R^2, R^4, R^5, R^6, R^7$ and $R^8$ are as defined for formula I, in fully or partly functional group protected form, with a nitrogen compound of the general formula IV

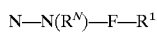

$$\text{N—N(R}^N\text{)—F—R}^1 \qquad\qquad \text{IV}$$

wherein $R^1$, F and $R^N$ are as defined for formula I;
and optionally fully or partly deprotecting the product thereby obtained in order to obtain a compound of the general formula I.

Preferably the compound of the general formula III is used in its activated ester form. In particular, the reaction between the carboxylic acid compound of the general formula III and the nitrogen compound IV is facilitated by using a coupling reagent such as one of those mentioned further above.

Thus, the present invention also provides a compound of the formula I for the preparation of an assay device for the detection of antibodies against Gram-negative bacteria and/or O-antigens of Gram-negative bacteria.

The present invention further provides a compound of the formula I for the preparation of a solid surface carrying an immobilised polysaccharide.

Analysis of polysaccharide reporter group conjugates

It is often valuable to be able to asses the quality of the reporter group polysaccharide conjugates prior to immobilisation to solid surfaces. Appropriate analytical protocols must be available to ensure that immunogenic epitopes on the polysaccharide are intact after conjugation to the reporter molecule and at the same time to ensure that the conjugates are produced in a reproducible manner.

In connection with the present invention, a UV spectroscopic method that can be used to asses the amount of reporter groups attached to the polysaccharide as well as to asses the amount of DNA and protein present in the polysaccharide reporter group preparations has been developed. Thus, as described in the Experimental section, measurement of the absorption at 260 and 280 nm can be used to asses the amount of DNA and protein, while the amount of reporter groups attached to the polysaccharide can be assessed at a wavelength specific to the reporter group. Competitive ELISA and indirect ELISA as described in the Experimental section is a powerful tool to quantify the presence of intact immunogenic epitopes in different polysaccharide reporter group conjugate preparations. Thus, the combination of the two developed analytical techniques ensures that different batches of polysaccharide reporter group preparations can be quality controlled. The final decisive analytical protocol is the quantitative measurement of the ability to immobilise of the polysaccharide reporter group conjugates. These procedures are outlined below and in the Experimental section.

Immobilisation of polysaccharide reporter molecule conjugates

In a subsequent step of the method according to the present invention, the polysaccharide-report molecule conjugate is immobilised to the solid surface by forming a specific bond between the recognition/substrate site of said reporter molecule and a reception/reagent site of the solid surface.

The term "forming a specific bond" is intended to mean the establishment of a covalent bond between the reporter part of the polysaccharide/reporter molecule conjugate and the solid surface as well as establishment of a non-covalent bond involving an affinity pair.

In one aspect of this invention the reporter part is a photochemically reactive group that is capable of forming a covalent bond to a solid surface upon irradiation with light. Examples of photochemically reactive groups are substituted coumarins, benzofurans, indols, angelicins and in particular psoralens as disclosed in EP 0 319 957. A number of patent publications U.S. Pat. Nos. 4,722,906, 4,973,493, 5,002,582 and PCT/US88/04491 disclose photochemically reactive groups selected from carbene and nitrene precursers and ketones that are able to form covalent bonds to solid surfaces upon irradiation with light. A particular preferred subclass of photochemically reactive groups are quinones such as those disclosed in WO 96/31557, e.g. anthraquinones (AQ), benzoquinones and phenanthraquinones. A particularly interesting photochemically reactive group is the anthraquinone group.

The photochemical formation of the covalent bond to the solid surface typically comprises of the following steps: The polysaccharide reporter molecule conjugate (PS-RM) is brought into solution in an appropriate solvent. Preferentially, the solvent is water, or a mixture of water and a water miscible organic solvent such as N,N-dimethyl formamide, dimethyl sulfoxide, dioxane, methanol, ethanol and acetone or the pure organic solvent. The solvent or solvent mixture is selected to ensure the solubility of the polysaccharide reporter molecule conjugate but at the same time allowing the best conditions for the subsequent immobilisation step. Using water or a mixture of water and a water miscible organic solvent, inorganic salts may be added to enhance the photochemical coupling step to the solid surface and to control the pH of the solution. As demonstrated in the Experimental section the exact nature of the salts as well as the concentration of the polysaccharide reporter molecule conjugate and pH of the solution are parameters which can be adjusted in order to obtain improved results. Often, the photochemical process require (or is facilitated by) a carbon-containing surface.

The solution of the polysaccharide reporter molecule conjugate is brought into contact with the solid surface while still in solution, and is exposed to light of a suitable wavelength. Preferentially, the wavelength is chosen between 200 and 700 nm but depends on the specific photochemically reactive group chosen. For anthraquinones, the wave length is typically 300–400 nm. Irradiation time varies depending on the nature of the polysaccharide reporter molecule conjugate but preferentially irradiation times should be less than 200 minutes. Alternatively, the solution of the polysaccharide reporter molecule conjugate is brought into contact with the solid surface, the solvent or solvent mixture is evaporated and the conjugate is finally exposed to light as described above. In both instances rinsing with water or a suitable water/solvent mixture is used afterwards to remove non-covalently bound conjugates.

In a second aspect of this invention the reporter part is a thermochemically reactive group that is capable of forming a covalent bond in a chemoselective manner to a solid surface having a suitable functional group. Examples of thermochemically reactive groups are carboxylic acids, primary amines, secondary amines, acid hydrazides, semicarbazides, thiosemicarbazides, thiols, aliphatic hydrazines, aromatic hydrazines, epoxides and maleimides. Often, the thermochemical process require (or is facilitated by) a carbon-containing surface.

The polysaccharide reporter molecule conjugate (PS-RM) is brought into solution in an appropriate solvent. Preferentially the solvent is water, or a mixture of water and an water miscible organic solvent such as N,N-dimethyl formamide, dimethyl sulfoxide, dioxane, methanol, ethanol and acetone or the pure organic solvent. The solvent or solvent mixture is selected to ensure the solubility of the polysaccharide reporter molecule conjugate but at the same time allowing the best conditions for the subsequent immobilisation step.

The solution of the polysaccharide reporter molecule conjugate is brought into contact with the solid surface in order to facilitate the covalent bond formation. Addition of additional coupling reagents may be necessary in order to promote the covalent bond formation. In most cases it is very important to control the pH during the covalent bond formation. In aqueous solution or in mixture of water and a water miscible solvent this can be achieved using standard buffers. In organic solvents this can be achieved by the use of suitable organic or inorganic acids and bases that are selected according to their solubility in the solvent as well as according to their relative acid or base strength. In all cases the precise conditions are chosen to promote the covalent coupling while at the same time preserving the integrity of the polysaccharide and the reporter molecule. In most cases the covalent bond formation is allowed to proceed without evaporation of the solvent, but in certain cases evaporation can be advantageous. Many varieties of such methods exist and are well known to the person skilled in the art (Greg T. Hermanson et. al., Immobilized Affinity Ligand Techniques, Academic Press Inc., 1992).

In a third aspect of this invention the reporter molecule is one part of an affinity pair. Affinity pairs are well known to the person skilled in the art (Greg T. Hermanson et. al., Immobilized Affinity Ligand Techniques, Academic Press Inc., 1992) and illustrative examples are biotin/avidin, biotin/streptavidin, biotin/NeutrAvidin, glutathione/glutathione-S-transferase, iminodiacetic acid metal complex/hexa-histidine tagged peptides and proteins, nitrilotriacetic acid metal complex/hexa-histidine tagged peptides and proteins, DNA/DNA, DNA/RNA, RNA/RNA and mono- or polyclonal antibodies raised against specific haptens/hapten. An especially intriguing example of an affinity pair is two complementary strands of locked nucleic acids (L N A, Nielsen et al., Chem. Commun., 1997, 9, 825–6.). Preferably, the part of the affinity pair used to prepare the polysaccharide reporter group conjugate is a low molecular to medium molecular weight compound preferably less than 10,000 most preferably less than 7,000.

The polysaccharide reporter molecule conjugate is brought into solution in an appropriate solvent. Preferentially the solvent is water, or a mixture of water and an water miscible organic solvent such as N,N-dimethyl formamide, dimethyl sulfoxide, methanol, ethanol and acetone or the pure organic solvent. The solvent or solvent mixture is selected to ensure the solubility of the polysaccharide reporter molecule conjugate but at the same time allowing the best conditions for the subsequent immobilisation step. The solution of the polysaccharide reporter molecule conjugate is brought into contact with the solid surface that has been pre-coated with the second part of the affinity pair. In most cases it is necessary control the pH, the nature and concentration of ions in the solution and in many cases it may be necessary to add detergents in order to optimise the immobilisation step. Many varieties of such methods are well known to the person skilled in the art (Greg T. Hermanson et. al., Immobilized Affinity Ligand Techniques, Academic Press Inc., 1992).

One very important property of the methods disclosed herein is that they enable the immobilisation of mixtures of more than one polysaccharide reporter group conjugate at the same time to the same surface in a well defined manner. As described in the Experimental section, the immobilisation of polysaccharide reporter group conjugates can be optimised individually and then finally be performed in a mixed reaction to create applications based on the mixed conjugates. The individual ratios of the immobilised conjugates can be easily optimised according to the specific application.

The solid surface to which the polysaccharide is to be attached can be selected from a wide variety of solid surfaces used in the analytical and diagnostic fields. The most interesting types of solid surfaces are those of organic polymers, glasses, silicium and silicium oxide (silica) as well as composite materials thereof.

Among the organic polymers, polystyrene, polycarbonate, polypropylene, polyethylene, cellulose, nitrocellulose, agarose, polyethyleneglycol terephthalate, polyvinylacetate, polyvinyldifluoride, polymethylpentene, polyvinylpyrrolidinone, polyacrylate, polyacrylonitrile, polymethylmethacrylate and polyvinylchloride are illustrative examples, where polystyrene and polycarbonate are especially interesting examples.

Among the glasses and ceramics, borosilicate glass (Pyrex glass) and soda-lime glass are especially relevant examples, e.g. in the form of specimen tubes, vials, and slides for microscopy.

The body in itself may have a form or may be designed and shaped for the particular desired use. E.g. the body may be in the form of a sheet, a film, a bead, a pellet, a disc, a plate, a ring, a rod, a net, a membrane, a filter, a tray, a microplate (a microtitre plate), a stick, or a multi-bladed stick. Especially interesting bodies to be coated according to the present invention are microplates (microtitre plates), e.g. polystyrene microplates (microtitre plates), sticks, slides, tubes and beads.

A further important property of the methods disclosed herein is the ability to perform the immobilisation of the polysaccharide reporter group conjugates in spatially addressable manner, which is very important in the development of bio-chips and bio-sensors and other miniaturised diagnostic systems. In these systems it is necessary that at least one component of the assay is immobilised at a well defined position. This will allow that each analytical component can be identified by the position, allowing the determination of many analytical components at the same time in one analytical sample.

It is also believed that the immobilisation of a polysaccharide may be performed according to an alternative method where a covalent bond is formed directly between the carboxy group of the polysaccharide and a chemical functionality attached to the solid surface, e.g. an amine, an aniline, a hydrazine, etc. In some instances commercially available solid surfaces may be used, e.g. the CovaLink microplates from Nunc, Denmark. It is believed that this method is less advantageous than the embodiments according to the main embodiments, in particular with respect to reproducibility. It is however believed that this alternative method might be useful for immobilisation of polysaccharides (PS) depleted the lipid part.

Thus, the present invention also provides a method for immobilising a polysaccharide (PS) to a solid surface, said polysaccharide having a keto-carboxy group (—C(=O)—COOH) or a ketal or hemiketal group corresponding thereto), by forming a covalent bond between the carboxy group of the polysaccharide and a chemical functionality of the solid surface.

It is evident from the above that the chemical functionality of the solid surface preferably should be of the same type as the those specified above resulting in essentially the same type of bond types between the polysaccharide and the solid surface as a specified above for the bond between the polysaccharide and the reporter molecule, i.e. a bond of the type PS'—C(=O)—N($R^N$)—F—L—SS, where PS', L, $R^N$ are as defined above and SS designates the solid surface. It should be understood that N($R^N$)—F—L may be part of the solid surface or whereto the polysaccharide is coupled or, alternatively, that N(R$^N$)—F—L may be coupled the polysaccharide prior to the coupling to the solid surface.

In summary, the present invention also provides solid surfaces obtained (or obtainable) according to the methods described above.

Applications of immobilised conjugates

The solid surfaces to which LPS derived polysaccharides are immobilised have various uses with the diagnostic and analytical fields, e.g. for the detection of Salmonella infections in various heards of animals, e.g. swine and poultry.

In a preferred embodiment, the immobilised Salmonella polysaccharides comprise O-antigens 1,4,5,6,7 and 12 represented by a mixture of anthraquinone-coupled LPS-derived polysaccharides of Salmonella Typhimurium and Salmonella Choleraesuis, coupled to the solid surface as an optimised mixture of the two polysaccharides as described in Example 24. This solid surface is intended for use in an immunoassay for antibodies against Salmonella spp. and for Salmonella O-antigens of the described serotypes, the immunoassay comprising contacting the surface with a sample, preferably a liquid sample such as serum, meat juice, milk or other biologically derived fluids. Antibodies are then detected by a detection antibody that comprises an enzyme label, the whole assay being performed as an enzyme-linked immunosorbent assay (ELISA). Other labels, e.g. fluorescent labels, labels for time-resolved fluorescent detection, radioactive labels in general, radio-labelled for proximity scintillation counting, may also be used.

The present invention provides the use of a solid surface carrying a polysaccharide immobilised as described above (or by other methods yielding the same result) in a diagnostic or antigen serotyping assay, preferably a diagnostic assay. The assay is preferably a solid phase immunoassay. In particular, the diagnostic assay is a serological assay, e.g. a serological assay for detection of antibodies against microorganisms such as Gram-negative bacteria. Especially, the diagnostic assay is a serological assay for detection of antibodies against Salmonella spp.

The present invention also provides an assay device for the detection of antibodies against one or more Gram-negative bacteria, comprising a solid surface having immobilised thereto a polysaccharide, said polysaccharide corresponding to the carbohydrate part of the bacterial lipopolysaccharide (LPS) of the Gram-negative bacteria via the carboxylic acid group of a KDO monosaccharide unit of said polysaccharide. The polysaccharide is preferably immobilised to the solid surface according to the method defined herein. The solid surface which is included in the assay device typically have a shape particularly suited for the assay in question. The assay device may furthermore include a protective sheet and may be accompanied by an instructions sheet.

Particularly interesting assay devices are those used for serotyping of bacteria and for antigen detection. Furthermore, assay devices including more than one type of PS immobilised to the surface of a device member constitute preferred embodiments.

The present invention also provides a method for estimating the number of a specific bacteria, for serotyping of bacteria and for antigen (LPS/PS) detection by utilising the assay devices described above. Particularly interesting embodiments involve the use of AQ-PS immobilised microplates. These diagnostic methods render it possible to detect even small amounts of bacteria in biological fluids and provides the determination of a bacteria serotype. This is particularly interesting and valuable for the detection of Salmonella and Actinobacillus infections.

EXPERIMENTAL

General

Chloroform, dimethyl sulfoxide (DMSO) and methanol were purchased from Labscan and were of HPLC purity, acetic acid (99–100%) from Riedel de Häen, water-soluble carbodiimide (WSC, 1-(3-dimethylaminopropyl)-3-ethyl carbodiimide) from NovaBiochem, N-hydroxy succinimide (96%) from Aldrich, "Slide-a-lyzer" from Pierce, H-βAla-βAla-(CH$_2$)$_3$—NHCO—AQ.HCl were synthesised as described earlier (WO 96/31557) (βAla means β-alanine). Dialysis tubes (MWCO: 6–8000) were purchased from Spectra/Por, polystyrene microplates (PolySorp) from Nunc. PBS: phosphate buffered saline, pH 7.2, 0.15 M NaCl. PBS, Tween: PBS+0.05% Tween 20. PBS, Tween, BSA: PBS-Tween+1% BSA (bovine serum albumin)). OPD-substrate solution: 0.1M citrate-phosphate buffer, pH 5.0, 0.66 mg/mL OPD (O-phenylene diamine), 0.012% H$_2$O$_2$. All swine sera were from the Danish Veterinary Laboratory.

EXAMPLE 1

Purification of lipopolysaccharide (LPS) from Salmonella Typhimurium and Salmonella Choleraesuis Culture. Salmonella Typhimurium no. 3389-1/92 (O: 1, 4, 5, 12) and Salmonella Choleraesuis var. Kunzendorf no. 143 (O: 6, 7) were used for the preparation of LPS. For plate culture, Columbia agar (Oxoid, Unipath Ltd., Basingstoke, UK) supplemented with 5% bovine blood (C-blood agar) was used as the solid growth medium. For broth culture, the bacteria were grown aerobically at 37° C. in flasks with shaking at 130 rpm. Strains were stored at −80° C. in LB-broth supplemented with 10% glycerol.

For fermentation, a 7 liter MBR Labor Bioreactor (MBR Bio Reactor AG, Switzerland) with 4 liter LB medium was inoculated with a 800 mL overnight broth culture. Temperature was maintained at 37° C. and pH was maintained at 7.2 throughout and aeration was set at 50% pO$_2$ automatically regulating by sparging sterile atmospheric air at constant agitation of 500 rpm. Foam was controlled by addition of silicon emulsion. 90 minutes after inoculation, 400 mL 25% glucose was added. Five hours after inoculation, aeration was reduced to approximately 1 liter pr. minute. After approximately 18 hours of cultivation, aeration was stopped and 150 mL of formalin was added to a final concentration of approximately 3% at 20° C. and 200 rpm and inactivation was continued for 20 hours under these conditions.

Inactivation of the culture was checked on C-blood agar 6 hours after the addition of formalin, incubating the inoculated C-blood agar plates overnight. If inactivation was found to be complete the inactivated culture was released for further processing.

Extraction: LPS was extracted from the formalin killed cultures by hot aqueous phenol extraction, as described by Hassan et al. 1990. Briefly, the bacteria in 5 L inactivated culture broth were washed in 3×4 L PBS, followed by 4 washings in 5–10 volumes of acetone at 20° C., dried and resuspended in Milli Q water. LPS was then extracted from this suspension by hot (65° C.) 45% aqueous phenol; an equal volume of preheated 90% aqueous phenol was added to the suspension whereafter the mixture was kept at 65–68° C. for 10 min. under gentle agitation. After cooling to 4° C. followed by centrifugation for 30 min at 10,000 g, the upper aqueous phase was carefully retrieved and dialysed against Milli Q water for at least 48 hrs (with 3 shifts) at 4° C. and subsequently freeze-dried.

The average yield of purified LPS from one batch of fermentor culture was 1700 mg dry-weight with a range of 1500–2200 mg. Purify was evaluated from SDS-gels (see Example 3) and UV-analysis measurements. As seen on FIG. 5 only residual amounts of proteins were seen on the gels. Extinction measurements at 280 nm showed that aqueous LPS solutions (5–10 mg/mL LPS) of LPS contained around 1.5 mg/mL protein. On silver stained SDS-PAGE (see Example 3) the typical ladder-like arrangement of bands is seen, indicating that the whole range of molecular weights has been retrieved.

EXAMPLE 2

UV-analysis of LPS

Figure 3:
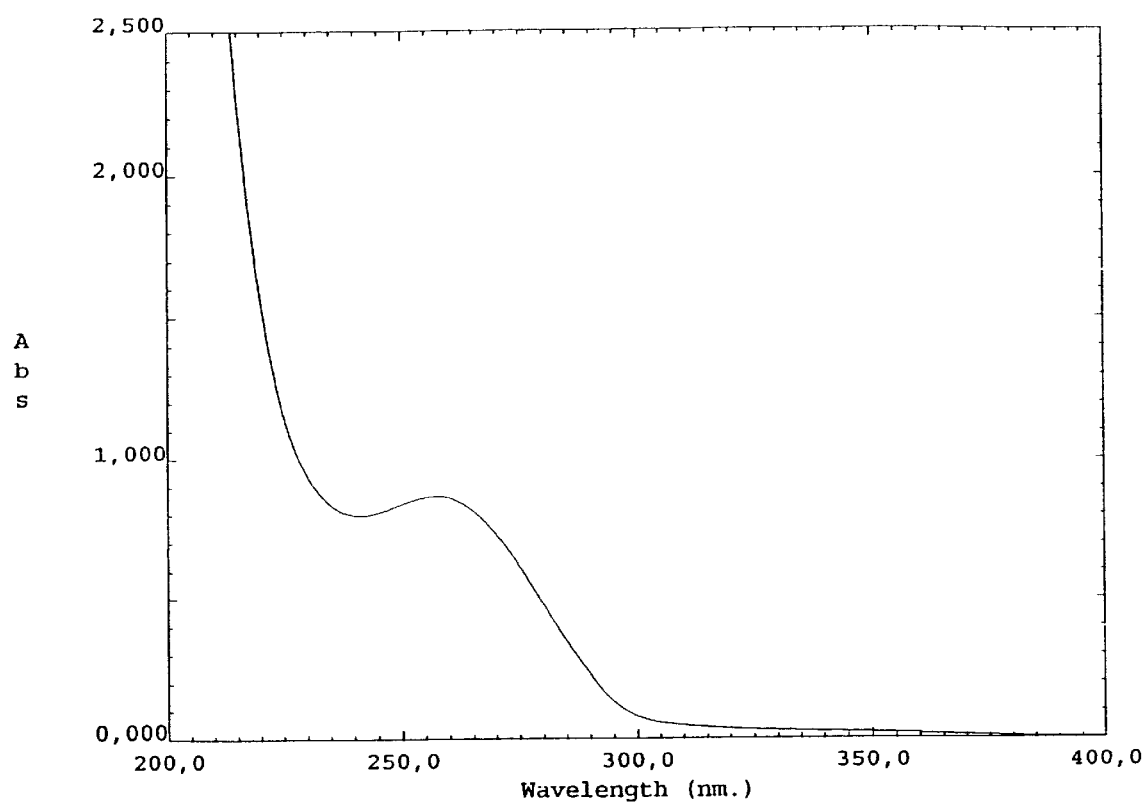
FIG. 3: UV spectroscopic profile of LPS from *Salmonella Typhimurium*.
Figure 4:
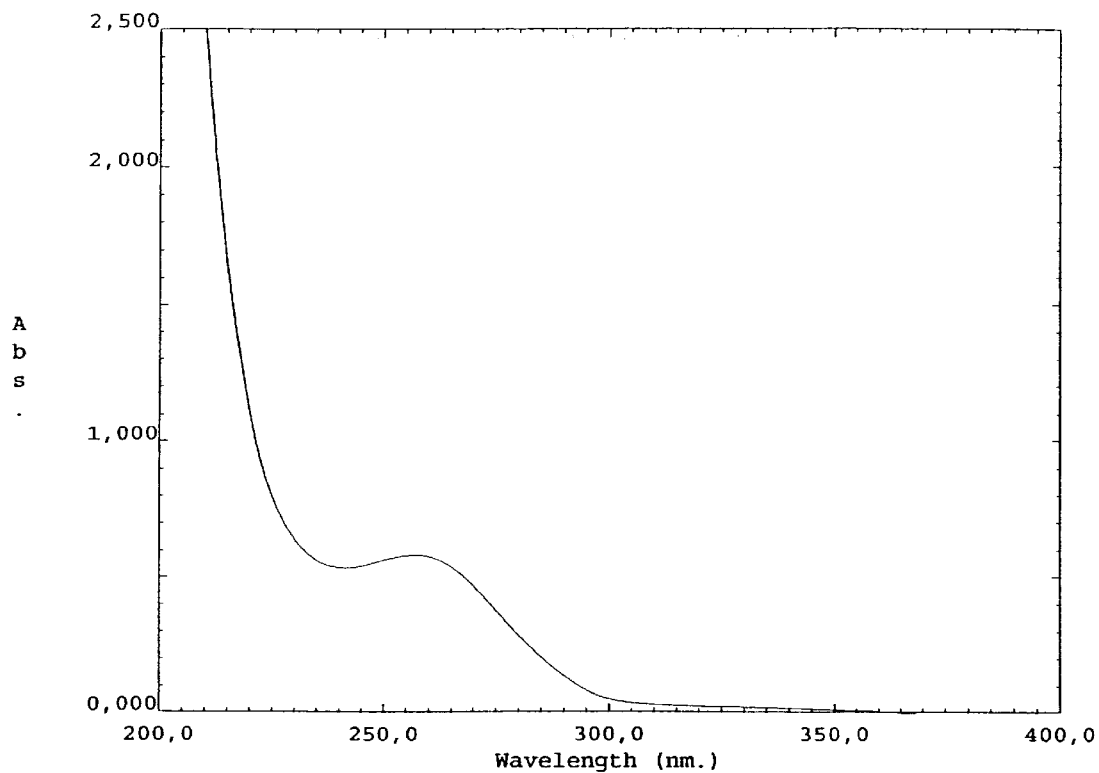
FIG. 4: UV spectroscopic profile of LPS from *Salmonella Choleraesuis*.

UV spectroscopy can be used to analyse the DNA and protein content of the LPS. DNA content can be measured at 260 nm and protein content at 280 nm. Briefly, the LPS is dissolved in ultra-pure water to a final concentration of 0.5 mg/mL. The UV spectrum is measured from 200–400 nm with ultra-pure water alone as the reference. FIG. 3 shows a typical UV-profile of LPS derived from Salmonella Typhimurium, while FIG. 4 shows a typical UV-profile of LPS derived from Salmonella Choleraesuis.

EXAMPLE 3

SDS-PAGE analysis of LPS

Sodium dodecyl sulfate polyacrylamide gel electrophoresis (SDS-PAGE) can be used for the analysis of LPS preparations for determination of the molecular weight distribution of the preparation. By this method smooth LPS preparations typically give a "ladder" of bands representing LPS molecules of increasing molecular weight, each separated by the molecular weight of the repeating unit of the O-polysaccharide. Polyacrylamide gels (12.5%) were run according to the method of Laemmli (Laemmli, U. K., 1970, Nature 227, 680–685, Cleavage of structural proteins during the assembly of the head of bacteriophage T4). The LPS was diluted in sample buffer to a final concentration of 2–4 mg/mL LPS (1% SDS) and boiled for 5 min, before being applied to the wells. For detection of proteins the gels were stained in 0.4% (w/w) Coomassie Brilliant Blue R250. For detection of LPS the gels were silver-stained according to the method of Tsai and Frasch (Tsai, C.-M., Frasch, C. E., 1982, Anal. Biochem. 119, 115–119, A sensitive silver stain for detecting lipopolysaccharides in Polyacrylamide gels).

Figure 5:
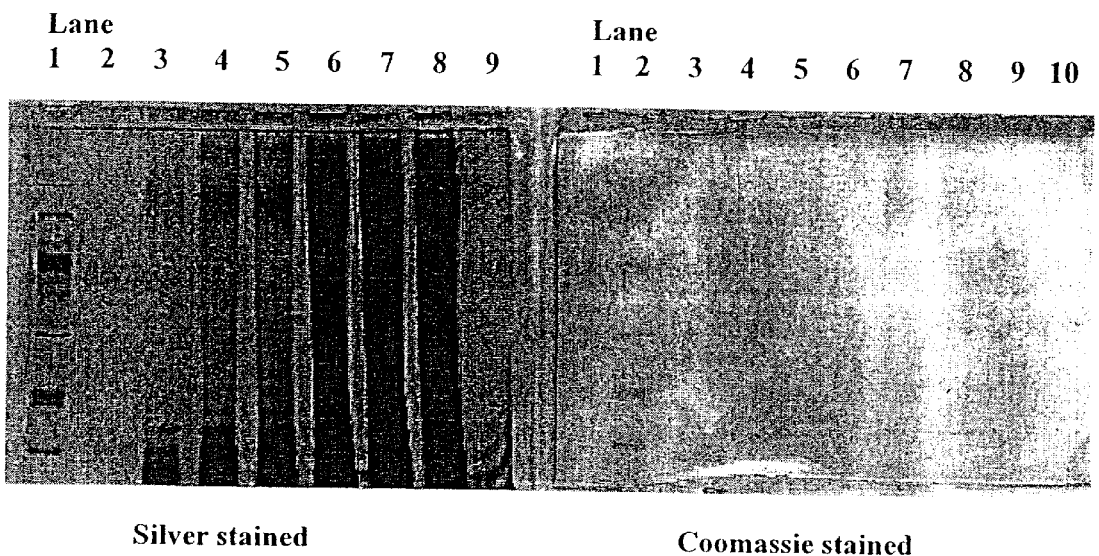
FIG. 5: Left: Silver stained polyacrylamide gel of purified LPS from *Salmonella Typhimurium*. Lane 1: Low molecular weight marker (BioRad); 2: Empty; 3: 4 µg LPS; 4: 8 µg LPS; 5: 12 µg LPS; 6: 16 µg LPS; 7: 20 µg LPS; 8: 24 µg LPS; 9: Empty. Right: Coomassie stained polyacrylamide gel of LPS from *Salmonella Typhimurium*. Samples applied as above.
Figure 6:
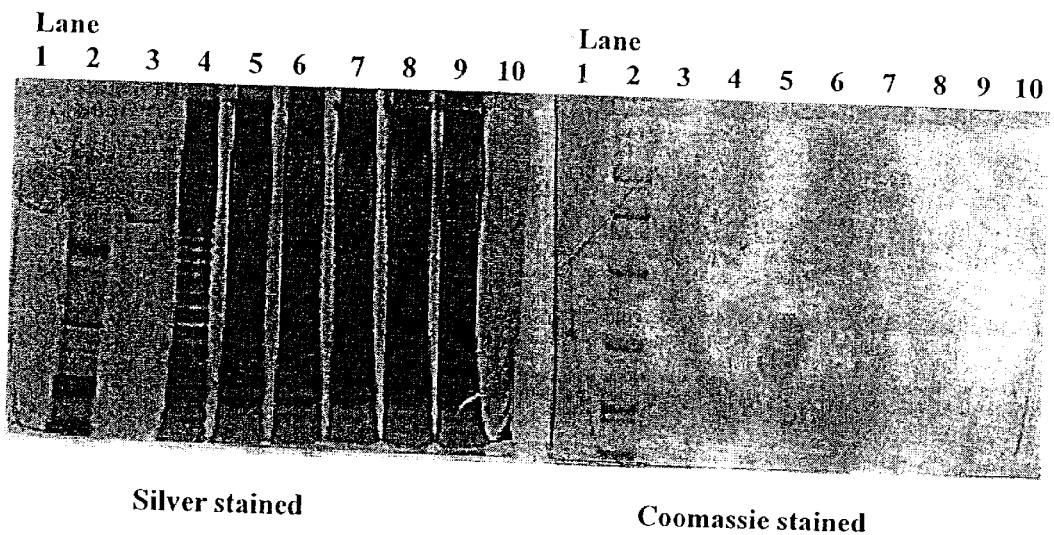
FIG. 6: Left: Silver stained polyacrylamide gel of purified LPS from *Salmonella Choleraesuis*. Lane 1: Empty; 2: Low molecular weight marker (BioRad); 3: Empty; 4: 6 µg LPS; 5: 12 µg LPS; 6: 18 µg LPS; 7: 24 µg LPS; 8: 30 µg LPS; 9: 36 µg LPS; 10: Empty. Right: Coomassie stained polyacrylamide gel of LPS from *Salmonella Choleraesuis*. Samples applied as above.

FIG. 5 shows a typical analysis of a Salmonella Typhimurium LPS preparation and FIG. 6 shows a typical analysis of a Salmonella Choleraesuis LPS preparation. As seen in the figures, only residual amounts of protein was visualised by the Coomassie Brilliant Blue stain, while on the silver stained gels the ladder-like arrangement of bands is seen indicating that the whole range of molecular weights has been retrieved.

EXAMPLE 4

Indirect ELISA for determination of LPS and PS

As intact LPS normally has the ability to bind passively to microplates via the hydrophobic lipid A-part of the molecule an indirect ELISA in which LPS is coated can be used to determine the amount of LPS in a certain LPS-preparation. In the same way the presence of intact LPS in a preparation of PS can be analysed by coating the PS preparation.

Figure 7:
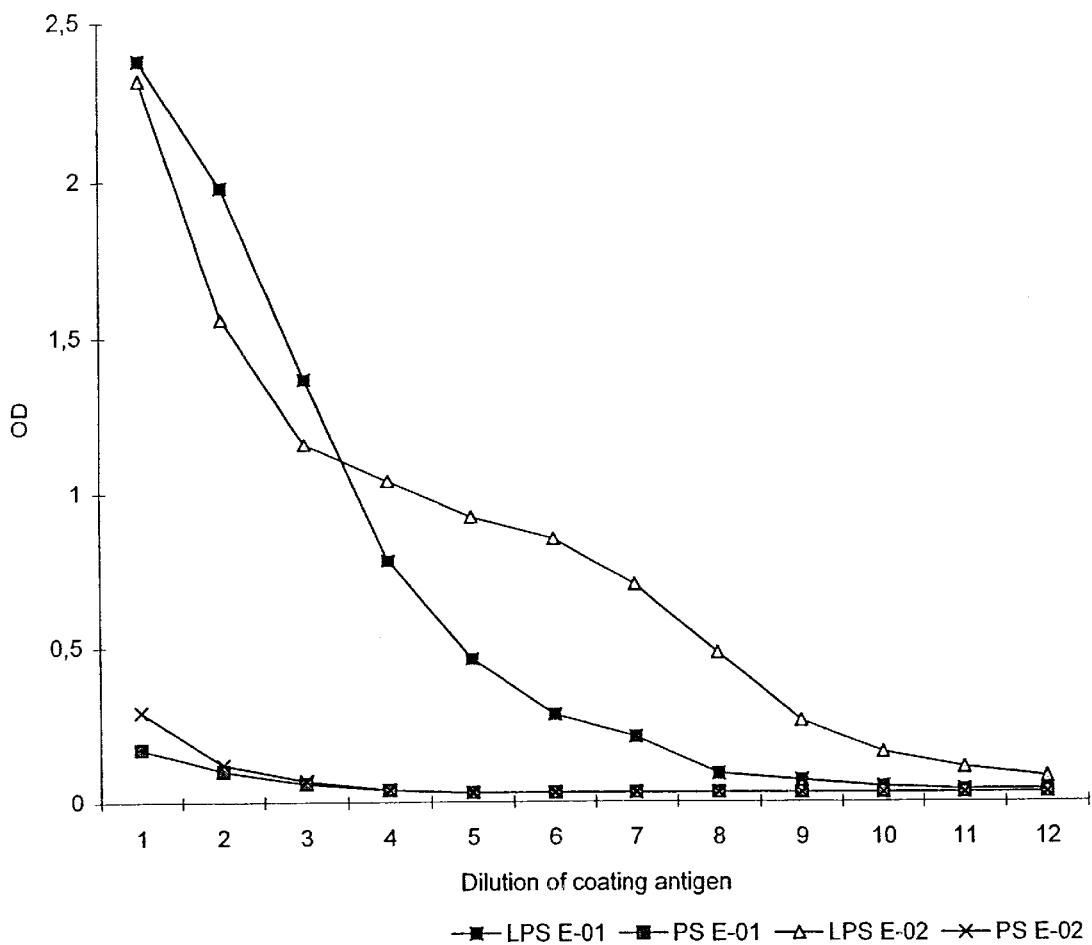
FIG. 7: Indirect ELISA of LPS and of PS from *Salmonella Typhimurium*. The antigens were coated in a 2-fold titration row starting from 0.4 µg/mL. A *Salmonella Typhimurium* positive swine serum diluted 1/400 was used as antibody. (Samples appear in the order (highest OD at "1" first): LPS E-01, LPS E-02, PS E-02, PS E-01.)

Indirect ELISA was performed essentially according to the protocol previously published by B. Nielsen et al. (1995), only omitting blocking of the plates. The plates were coated with a two-fold dilution series of the LPS or PS preparation typically starting at 0.05 mg/well in 0.1 M sodium carbonate, 1.0 M NaCl, pH 9.6 over night at 4° C. After washing in PBS, Tween either a standard monoclonal antibody directed against Salmonella Typhimurium O-antigens (MAB Hytest clone 1E6, 1 mg/mL, diluted 1/25000 in PBS, Tween, BSA) or a positive pig serum, diluted 1/400 in PBS, Tween, BSA. In FIG. 7 a positive pig serum is used. 100 µL was applied pr. well and incubated for 1 h at room temperature. The plates were then washed three times in PBS, Tween and subsequently incubated with HRP-conjugated rabbit anti mouse IgG (PO260 DAKO, diluted 1:2,000) with the MAb or HRP-conjugated rabbit anti swine IgG (PO164, DAKO diluted 1:2,000) with the swine serum; dilutions were done in PBS, Tween, BSA for 1 hour at room temperature. The plates were washed as before, and 100 µL OPD substrate solution was added to each well and incubated 10–15 min. The reaction was stopped with 100 µL 0.5 M $H_2SO_4$ and the optical density was read at 490 nm subtracting 650 nm for background correction.

Figure 8:
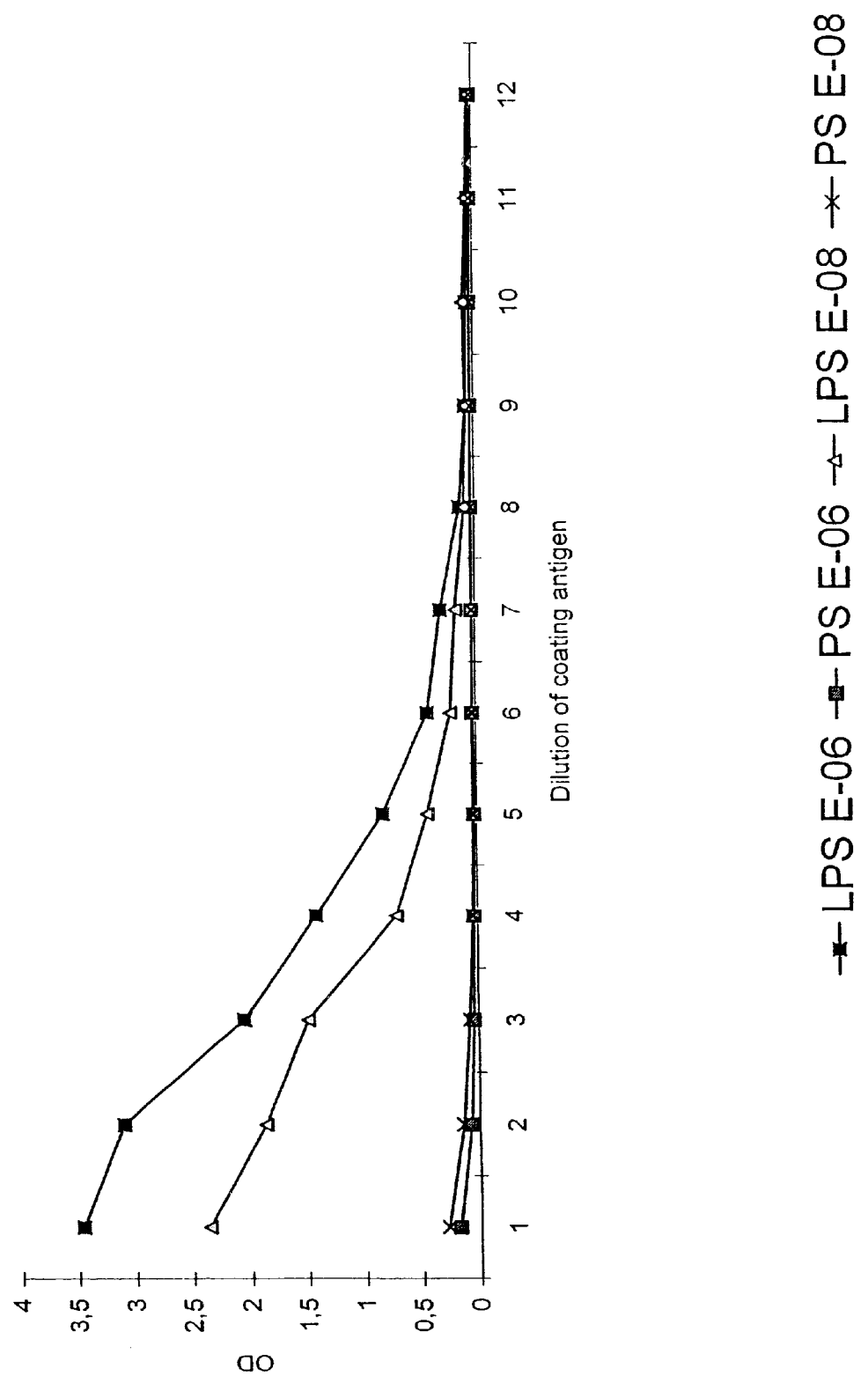
FIG. 8: Indirect ELISA of LPS and of PS from *Salmonella Choleraesuis*. The antigens were coated in a 2-fold titration row starting from 0.6 µg/mL. A *Salmonella Infantis* positive swine serum diluted 1/600 was used an antibody. (Samples appear in the order (highest OD at "1" first): LPS E-06, LPS E-08, PS E-08, PS E-06.)

FIG. 7 shows typical example of Salmonella Typhimurium LPS and PS preparation analysed by a positive swine serum as described above and FIG. 8 shows a corresponding analysis of a Salmonella Choleraesuis LPS preparation using an Infantis-positive swine serum. It is seen that the LPS-preparations bind to the plates and are specifically recognised by the antibody, allowing their quantitation when compared to a standard preparation, while PS exhibit very little binding to the plates.

EXAMPLE 5

Competitive ELISA determination of immunogenic epitopes in LPS and PS

The presence of intact immunogenic epitopes in different LPS preparations can be determined by competitive ELISA using a fixed concentration of intact LPS for coating and incubating the antigen (LPS or PS) preparation to be investigated together with the detection antibody. Apart from the presence of competitor, the ELISA is performed exactly as the indirect ELISA described in Example 4. Typically, a 2-fold titration from 5 mg/mL of the antigen is used and the competitive effect is seen as a reduction in the OD-level compared to the OD-level obtained in the absence of competing antigen.

Figure 13:
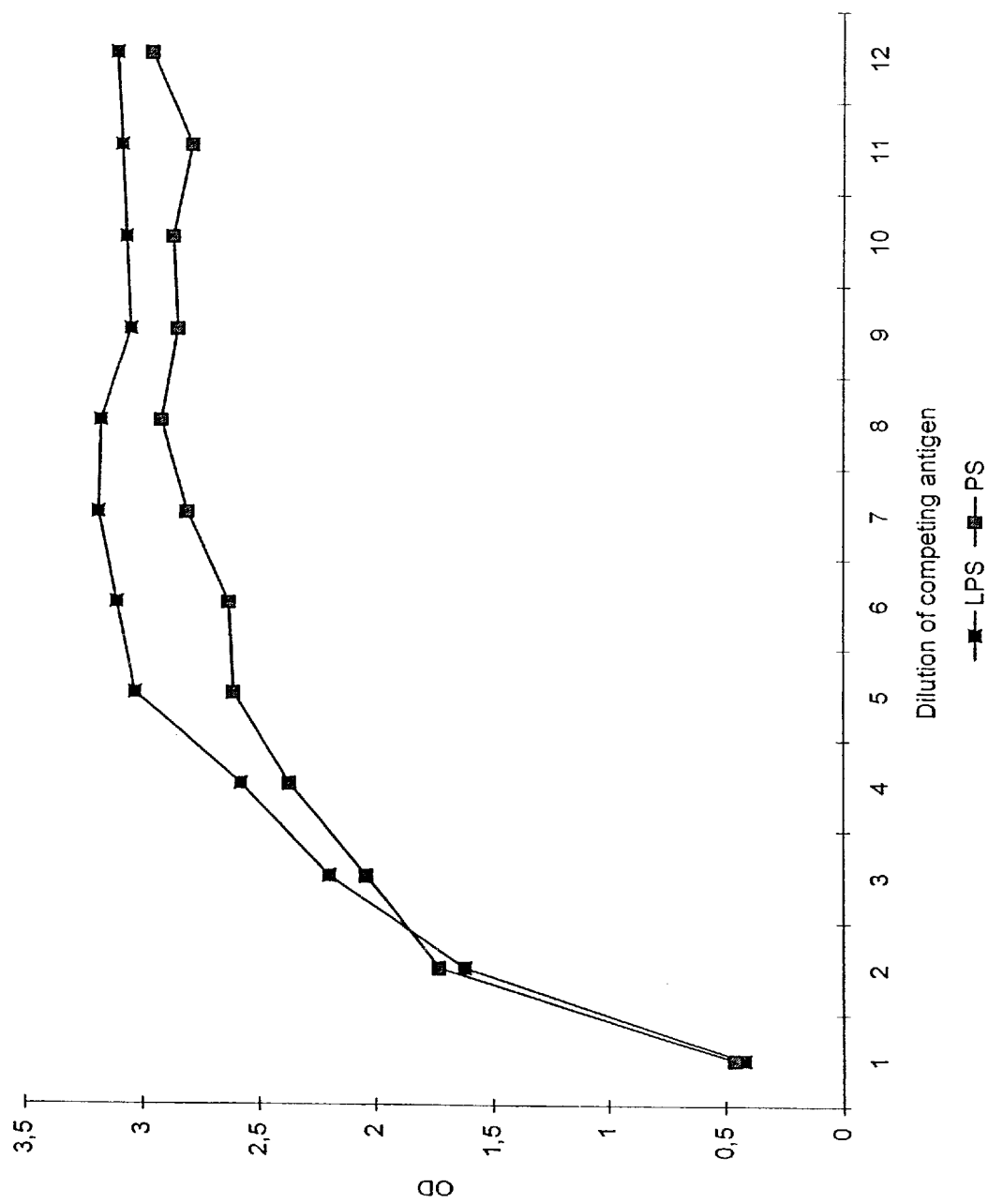
FIG. 13: Competitive ELISA of *Salmonella Typhimurium* PS 2-fold titrated on *Salmonella Typhimurium* LPS-coated plate, compared to the competition with intact *Salmonella Typhimurium* LPS. Both competitive antigens were titrated from 5 mg/mL. Plates were coated with *Salmonella Typhimurium* LPS at 0.05 µg/mL. A *Salmonella Typhimurium* positive swine serum was used as antibody at 1/400. (Upper curve: LPS, lower curve: PS.)
Figure 14:
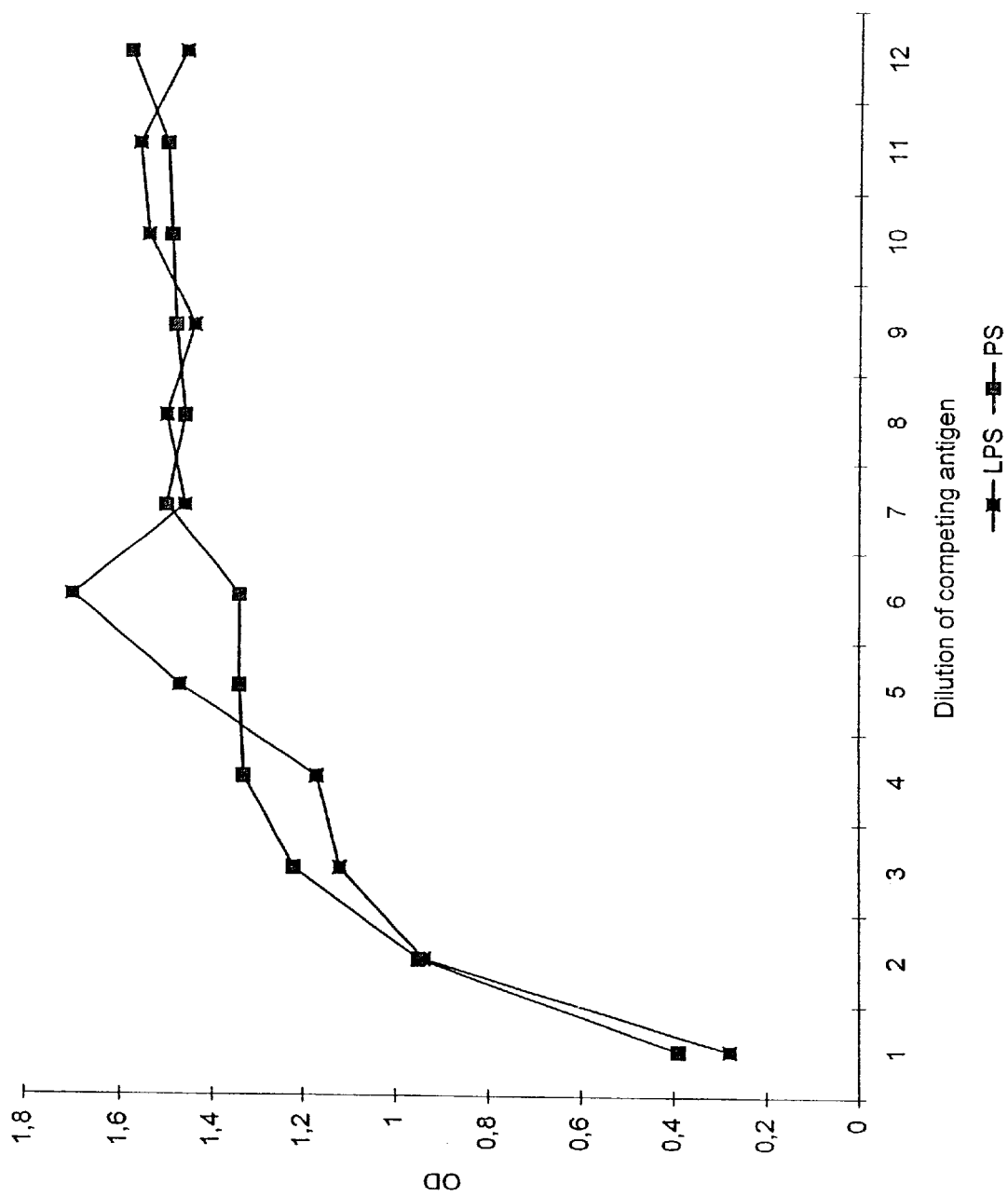
FIG. 14: Competitive ELIS of *Salmonella Choleraesuis* PS 2-fold titrated on *Salmonella Choleraesuis* LPS-coated plate, compared to the competition with intact *Salmonella Choleraesuis* LPS. Both competitive antigens were titrated from 5 mg/mL. Plates were coated with *Salmonella Choleraesuis* LPS at 0.5 µg/mL. A *Salmonella Choleraesuis* positive swine serum was used as antibody at 1/600. (Smoothest curve (and highest OD at 1 and 2): PS.)

FIG. 13 shows a typical result of the competition by a Salmonella Typhimurium PS preparation, using a Salmonella Typhimurium LPS coated microplate and a Salmonella Typhimurium LPS preparation as competitor control and detection by a Salmonella Typhimurium positive swine serum diluted 1/400 followed by HRP-conjugated rabbit-anti swine IgG (DAKO PO164, 1/2000), as detailed in Example 4. It is seen that the PS preparation at comparable concentrations is just as competitive as the intact LPS, indicating the preservation of antigenic epitopes in the PS. FIG. 14 depicts the same set-up with the Salmonella Choleraesuis antigens, using a positive swine serum at 1/600. Again, it is seen that the antigenicity of the PS preparation is preserved compared to the intact LPS.

EXAMPLE 6

Preparation of PS from LPS derived from Salmonella Typhimurium by delipidation Lyophilised LPS derived from Salmonella Typhimurium (1.55 g) is dissolved in ultrapure water (388 mL) then acetic acid (22 mL, 0.37 mol) is added. The mixture is divided into 40 mL portions in Nunc plastic tubes. The sealed tubes are heated in an oven (90° C., 60 minutes) followed by cooling in an ice bath for 10 minutes allowing the mixtures to reach room temperature. The mixtures are pooled and the combined aqueous phases extracted with chloroform/methanol (2:1 mixture v/v, 4×580 mL). The aqueous phase is subsequently dialysed at 4° C. against ultrapure water for 1–2 days (until the smell of phenol has disappeared) and finally lyophilised for 1–2 days giving the PS as a white solid. UV analysis (0.5 mg/mL) is performed as described in Example 2.

Yield: 0.520 g (34%), UV analysis: A(260 nm): 1.0; A(280 nm): 0.82.

EXAMPLE 7

Preparation of PS from LPS derived from Salmonella Choleraesuis by delipidation

Lyophilised LPS derived from Salmonella Choleraesuis (1.13 g) is dissolved in ultrapure water (283 mL) then acetic acid (16.2 mL, 0.27 mol) is added. The mixture is divided into 40 mL portions in Nunc plastic tubes. The sealed tubes are heated in an oven (90° C., 60 minutes) followed by cooling in an ice bath for 10 minutes allowing the mixtures to reach room temperature. The mixtures are pooled and the combined aqueous phases extracted with chloroform/methanol (2:1 mixture v/v, 4×425 mL). The aqueous phase is subsequently dialysed at 4° C. against ultrapure water for 1–2 days (until the smell of phenol has disappeared) and finally lyophilised for 1–2 days giving the PS as a white solid. UV analysis (0.5 mg/mL) is performed as described in Example 2.

Yield: 0.262 g (23%), UV analysis: A(260 nm): 1.52; A(280 nm): 1.09.

EXAMPLE 8

SDS-PAGE analysis of PS

Figure 9:
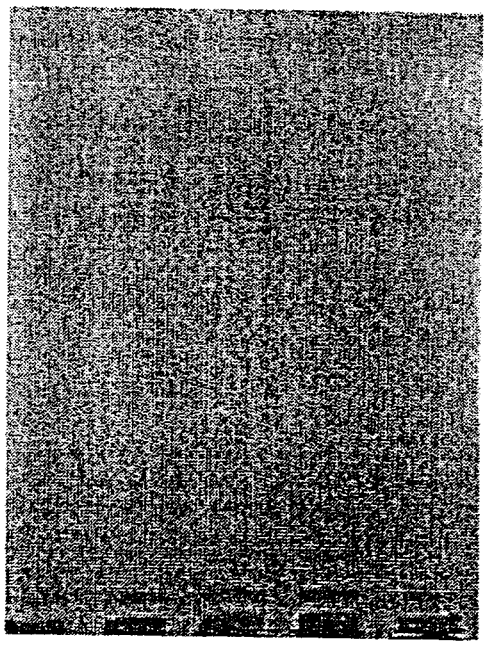
FIG. 9: Silver stained polyacrylamide gel of purified PS from *Salmonella Choleraesuis*. 1–5: Various batches of PS. 1.5 µg is applied.

SDS-PAGE visualised by silver staining can be used to analyse the PS derived by hydrolysis of LPS for the presence of residual LPS. As PS do not contain the lipidic. SDS-binding lipid A moiety, PS do not complex with SDS to form charged complexes that will move during the electrophoresis. Thus, pure PS will not give rise to bands in silver-stained SDS-PAGE. The SDS-PAGE of PS preparations is performed as described in Example 3. FIG. 9 shows typical results from five different Salmonella Choleraesuis PS preparations. As seen from the figure only minute amounts of LPS are still present in these PS preparations.

EXAMPLE 9

Determination of PS ability to passively bind to micro plates

PS derived from LPS by delipidation looses the ability to bind by passive adsorption to microplates. Thus PS preparations tested as described in Example 4 give rise to a very small OD signal as compared to a comparable amount of LPS, as seen with Salmonella Typhimurium and Salmonella Choleraesuis in FIGS. 7 and 8, respectively.

EXAMPLE 10

Preparation of *Actinobacillus pleuropneumoniae* PS.

Culture conditions. *Actinobacillus pleuropneumoniae* serotype 5b reference strain L20, and serotype 6 reference strain FEmø were used for preparation of the LPS-antigen. The strains were grown on meat broth agar plates supplemented with 5% bovine blood (Jacobsen, M. J. and Nielsen, J. P., 1995, Development of a selective and indicative medium for isolation of *Actinobacillus pleuropneumoniae* from tonsils. Vet.Microbiol. 47, 191–197) with a non-haemolytic *Staphylococcus aureus* as nicotinamide adenine dinucleotide (NAD) nurse-strain or on modified PPLO-agar plates (Nicolet, J., 1971, Zentralbl. Bacteriol. Abt. 1 Orig. 216, 487–495, Sur l'Hemophilose du porc III. Differenciation serologic de *Haemophilus parahaemolyticus*.) as solid media. Liquid growth medium for propagation of *A. pleuropneumoniae* consisted of 30 g/l Trypticase soy broth (BBL 11768, Becton Dickison, Cockeysville, Md., USA) supplemented with 10 g/l yeast extract (Oxoid L21, Unipath Ltd., Basingstoke, UK) and 0.03% (w/v) NAD (Sigma Chemical Co,. St. Louis, Mo., USA), pH 7.2 Liquid cultures of 1 l were grown in 2 l-Erlenmeyer shaking flasks at 37° C. with shaking at 130 rpm.

Extraction.

LPS was prepared from *Actinobacillus pleuropneumoniae* serotype 5b, strain L20 and serotype 6, strain Femφ by a method previously described (Nielsen, R., Andresen, L. O. and Plambeck, T., 1996, Serological characterization of *Actinobacillus pleuropneumoniae* biotype 1 strains antigenically related to both serotype 2 and 7. Acta Vet. Scand. 37, 327–336) except that the starting material was 10 g of wet-weight cells from liquid over night cultures and volumes were scaled proportionately. The LPS was precipitated as a gel by ultracentrifugation at 90,000 x g. The precipitated LPS was dissolved in 2 mL of deionised water and freeze dried.

Preparation of PS.

PS is prepared from the freeze-dried LPS of the two *Actinobacillus pleuropneumoniae* serotypes essentially as described in Example 6 and 7 for Salmonella PS. Yields of PS are expected to be in the 10–40% range, compared to starting amount of LPS.

EXAMPLE 11

UV-analysis of AQ-PS conjugates

Figure 10:
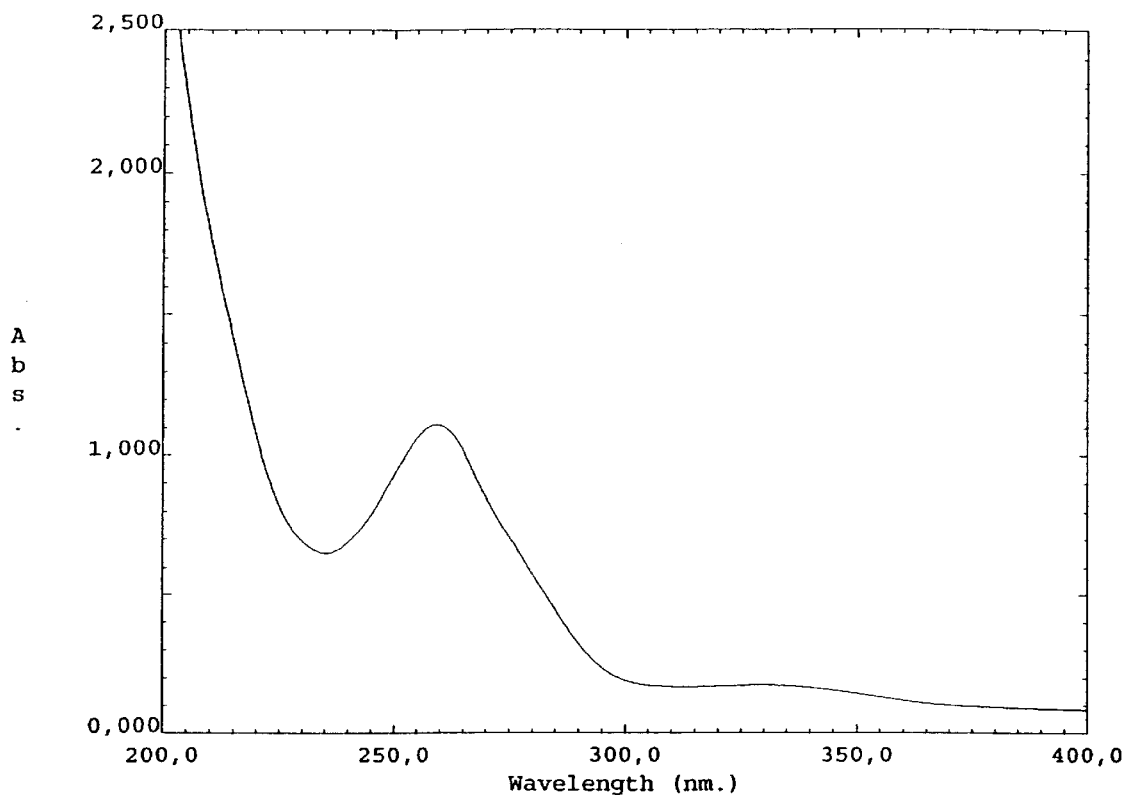
FIG. 10: UV spectroscopic profile of AQ-PS from *Salmonella Typhimurium*.
Figure 11:
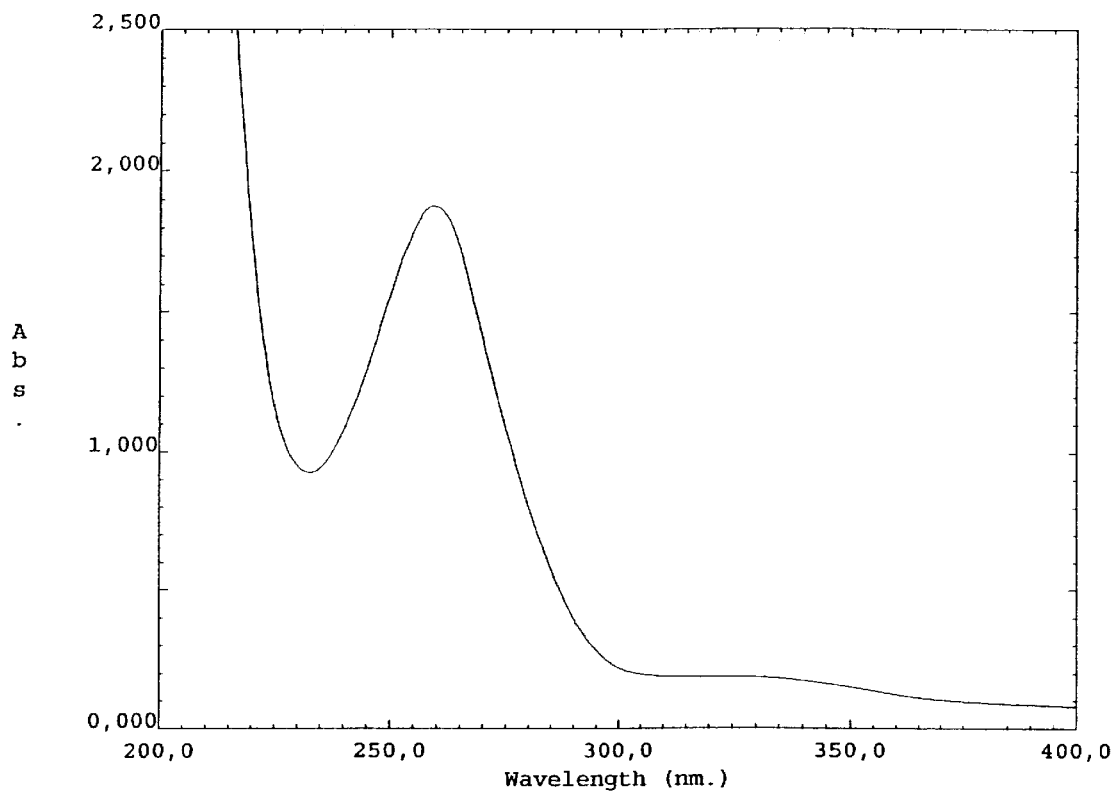
FIG. 11: UV spectroscopic profile of AQ-PS from *Salmonella Choleraesuis*.

UV spectroscopy can be used to analyse the AQ, DNA and protein content of the PS DNA content can be measured at 260 nm and protein content at 280 nm while the AQ content can be measured at 260 nm 280 nm and 330 nm (see "Spectroscopic methods in organic chemistry, 3'd ed., p 31", D. H. Williams and I. Fleming, McGraw-Hill (UK) 1980). Briefly, the AQ-PS is dissolved in ultrapure water to a final concentration of 0.5 mg/mL. The UV spectrum is measured from 200–400 nm with ultrapure water alone as the reference. FIG. 10 shows a typical UV-profile of AQ-PS derived from Salmonella Typhimurium, while FIG. 11 shows a typical UV-profile of AQ-PS derived from Salmonella Choleraesuis.

EXAMPLE 12

Conjugation of H-βAla-βAla-(CH$_2$)$_3$-NHCO-AQ . HCl to PS derived from Salmonella Typhimurium Make up following coupling buffer and freshly prepared solutions of reagents:

Solution 1: 1 mM N-hydroxy succinimide in DMSO (6 mg N-hydroxy succinimide dissolved in 50 mL DMSO).

Solution 2: 2 mM WSC in ultrapure water (10 mg WSC dissolved in 25 mL water).

Solution 3: 2 mM of reportergroup in ultrapure water (for H-βAla-βAla-(CH$_2$)$_3$-NHCO-AQ . HCl dissolve 24 mg in 25 mL water).

Buffer: Sodium hydrogen carbonate buffer, pH 8.0 (sodium hydrogen carbonate (8.4 g) is dissolved in ultrapure water and the pH adjusted to 8.0 with 1M aqueous HCl).

Weigh out PS derived from Salmonella Typhimurium (50 mg) into a round bottomed flask. Add solution 1 (3.13 mL) followed by the addition of solution 2 (1.56 mL), solution 3 (1.56 mL) followed by buffer (6.25 mL). The resultant clear solution is stirred over night at 4° C. The reaction mixture is subsequently dialysed against ultrapure water for three days at 4° C., changing the ultrapure water every day, and finally lyophilised for one day to the PS-AQ conjugate as a white solid. The preparation may include AQ-LPS conjugate as well depending on the amount of intact LPS in the PS preparation. Yield: 83%; UV analysis: A (260 nm): 1.11; A (280): 0.57: A (330 nm): 0.17

EXAMPLE 12a

Conjugation of H-βAla-βAla-(CH$_2$)$_3$-NHCO-AQ . HCl to PS derived from *Actinobacillus pleuropneumoniae* serotype 5b The solutions 1–3 are as described in Example 12.

Weigh out PS derived from *Actinobacillus pleuropneumoniae* 5b (App5b) 2 mg, 0.025 mmol - from Example 10) into a round bottomed flask. Add solution 1 (0.125 mL) followed by the addition of solution 2 (0.063 mL), solution 3 (0.063 mL) followed by buffer (0.25 mL). The resultant clear solution is stirred over night at 4° C. The reaction mixture is subsequently dialyzed against ultrapure water for three days, changing the ultrapure water once a day. The PS-AQ solution is lyophilized for one day, whereby the PS-AQ conjugate is obtained as white solid. The preparations may include minor amounts of AQ-LPS conjugate as well depending on the amount of intact LPS in the PS preparation.

EXAMPLE 13

Conjugation of H-βAla-βAla-(CH$_2$)$_3$-NHCO-AQ . HCl to PS derived from Salmonella Choleraesuis Weigh out PS derived from Salmonella Choleraesuis (50 mg) into a round bottomed flask. Add solution 1 (3.13 mL) followed by the addition of solution 2 (1.56 mL), solution 3 (1.56 mL) followed by buffer (6.25 mL). The resultant clear solution is stirred over night at 4° C. The reaction mixture is subsequently dialysed against ultrapure water for three days at 4° C., changing the ultrapure water every day, and finally lyophilised for one day to the PS-AQ conjugate as a white solid. The preparation may include AQ-LPS conjugate as well depending on the amount of intact LPS in the PS preparation. Yield: 66%; UV analysis: A (260 nm): 1.29; A (280 nm): 0.58; A (330 nm): 0.15.

EXAMPLE 14

Conjugation of H-βAla-βAla-(CH$_2$)$_3$-NHCO-AQ . HCl to PS derived from Salmonella Infantis Weigh out derived from Salmonella Infantis (2 mg) into a round bottomed flask. Add solution 1 (0.125 mL) followed by the addition of solution 2 (0.063 mL), solution 3 (0.063 mL) followed by buffer (0.25 mL). The resultant clear solution is stirred over night at 4° C. The reaction mixture is subsequently dialysed against ultrapure water for three days at 4° C., changing the ultrapure water every day, and finally lyophilised for one day to the PS-AQ conjugate as a white solid. The preparation may include AQ-LPS conjugate as well depending on the amount of intact LPS in the PS preparation.

EXAMPLE 15

SDS-PAGE analysis of AQ-PS

Figure 12:
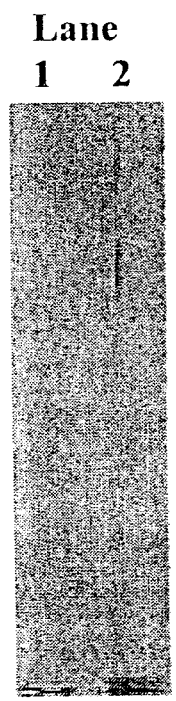
FIG. 12: Silver stained polyacrylamide gel of AQ-PS from *Salmonella Choleraesuis*. 1–2: Two different batches of AQ-PS. 1.5 µg is applied.

SDS-PAGE visualised by silver staining can be used to analyse the AQ-PS conjugate for the amount of AQ-LPS conjugate present. The AQ-PS preparations are tested by SDS-PAGE as described in Example 3. FIG. 12 shows typical result from two Salmonella Choleraesuis AQ-PS preparations.

EXAMPLE 16

Competitive ELISA determination of immunogenic epitopes in AQ-PS and AQ-LPS

The presence of intact immunogenic epitopes in different AQ-PS or AQ-LPS preparations can be determined by competitive ELISA on a LPS-coated microplate. Thus, the different AQ-PS/AQ-LPS preparations are tested essentially as described in Example 5 by incubating a two-fold dilution series of the AQ-PS/AQ-LPS together with the detection antibody. The plate is treated and read as described in Example 5. The result of this analysis was that increasing amounts of AQ-PS added to the plates result in decreasing signals due to increasing competition by the added AQ-PS for the antibody. This indicated that the antigenicity of LPS and PS is still preserved in AQ-PS.

EXAMPLE 17

Photochemical coupling of AQ-PS and AQ-LPS to polystyrene microplates. General procedure The lyophilised AQ-PS/AQ-LPS conjugates are dissolved in ultrapure water to a final concentration of 1 mg/mL. These stock solutions of conjugates have a long term stability (more than 3 months) when stored at 4° C. protected from direct light. Prior to photo-coupling the stock solutions are diluted into a 0.1 M solution of MgCl$_2$ in demineralised water. The final optimum concentration of each individual conjugate, the pH during photocoupling and the presence of inorganic salts must be determined individually for each application (see Examples 18 and 19). The very dilute photocoupling solutions should be carefully protected against direct sunlight. The diluted solutions of conjugates are added to each well of a polystyrene microplate (100 μl/well). The plate is placed below an appropriate UV light source and subsequently irradiated with UV light for 20 minutes Recommended UV-light sources are Philips HPA 400 (the lamp emits low energy UV-A and UV-B light mainly between 300 and 400 nm (WO 96/31557)) or Philips 25W-S fluorescent tubes that emit UV light between 310 and 400 nm with a maximum output at 345 nm. The optimum conditions for the UV-irradiation as well as irradiation time (see Example 20) must be optimised depending on the UV-light source and equipment used. After UV-irradiation the plate is aspirated, washed with demineralised water (3×300 μl) and finally dried at 37° C. for 30 minutes. The dry plates should be stored at room temperature in the dark.

EXAMPLE 18

Effect of AQ-PS/AQ-LPS conjugate concentration on photocoupling efficiency

The AQ-PS/AQ-LPS from Salmonella Typhimurium or Salmonella Choleraesuis is immobilised in different concentrations onto the microplates in order to determine the efficiency of the UV irradiation to immobilise the conjugates.

Make a stock solution of AQ-PS/AQ-LPS conjugate derived from Salmonella Typhimurium and Salmonella Choleraesuis as described in Example 17 and dilute each conjugate into separate tubes to a final concentration of 1000, 750, 500, 250 and 100 ng/mL Salmonella Typhimurium and 1000, 750, 500, 250 and 100 ng/ml for Salmonella Choleraesuis. As negative control 0.1 M MgCl is used. Add the 5 individual solutions of Salmonella Typhimurium conjugates to column 1–2, 3–4, 5–6, 7–8 and 9–10 of a polystyrene microplate (100 μl/well) and add 0.1 M MgCl to column 11–12. Add the 5 individual solutions of Salmonella Choleraesuis conjugates to column 1–2, 3–4, 5–6, 7–8 and 9–10 of a polystyrene microplate (100 μl/well) and add 0.1 M MgCl to column 11–12. Place the microplates below the UV-light source and irradiate for 20 min. Following UV-irradiation aspirate the plate, wash with demineralised water (4×300 μl) and assay directly without drying. Add Salmonella Typhimurium positive reference pig sera diluted in PBS, Tween, BSA (1:400) to each well of rows A–B, Salmonella Typhimurium negative reference pig sera diluted in PBS, Tween, BSA (1:400) to each well of rows C–D of the first plate (100 μl/well). Add Salmonella Choleraesuis positive reference pig sera diluted in PBS, Tween, BSA (1:400) to each well of rows A–B. Salmonella Choleraesuis negative pig reference sera diluted in PBS, Tween, BSA (1:400) to each well of rows C–D, of the second plate (100 μl/well). Incubate at room temperature with gentle agitation for 60 min., aspirate and wash all wells with PBS-Tween (3×300 μl) Add a HRP-labelled rabbit anti-swine IgG (DAKO PO164) diluted in PBS, Tween, BSA (1:2000) to each well. Incubate for 60 minutes at room temperature with gentle agitation, wash the wells and add OPD-substrate solution to each well of the plate (100 μl/well). Incubate the plate for 20 min. in the dark and stop the enzyme reaction by the addition of 0.5 M $H_2SO_4$ (100 μl/well). Read the results on a ELISA reader at 492 nm.

Figure 15:
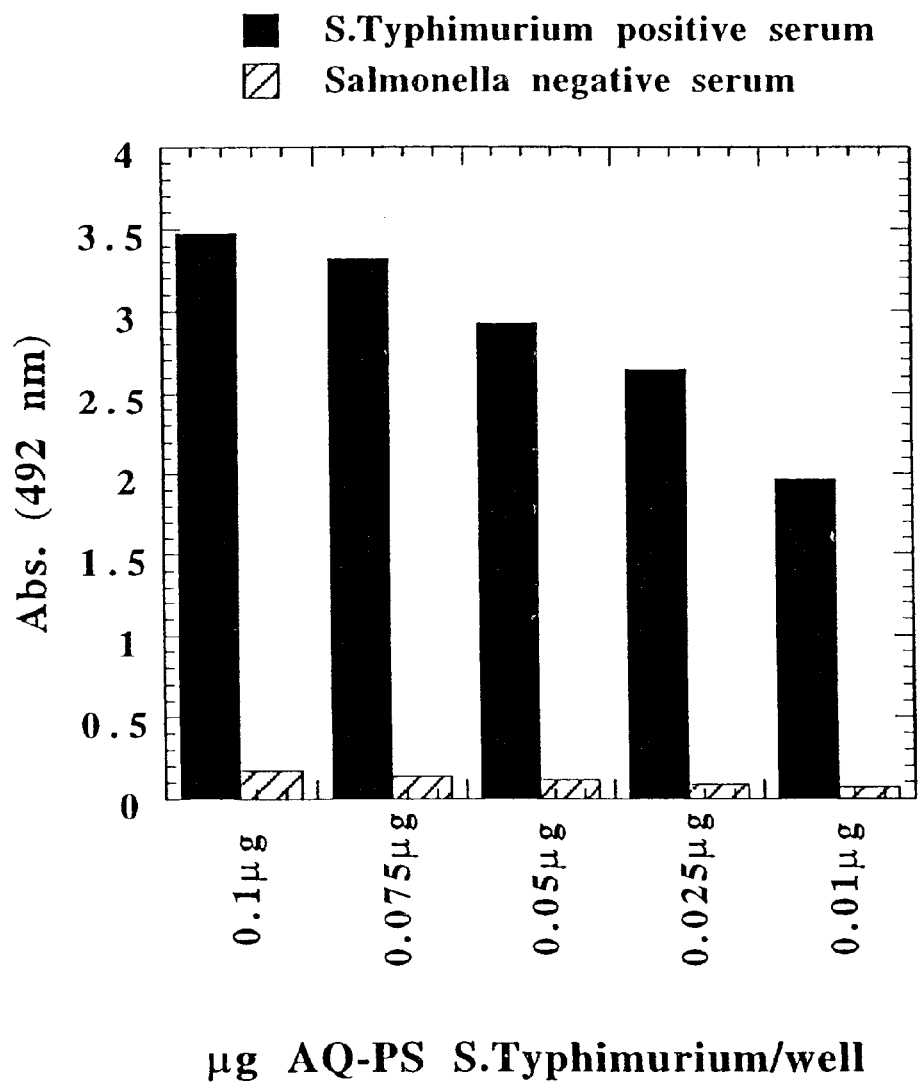
FIG. 15: Effect of AQ-PS (*Salmonella Typhimurium*) concentration on photocoupling efficiency.
Figure 16:
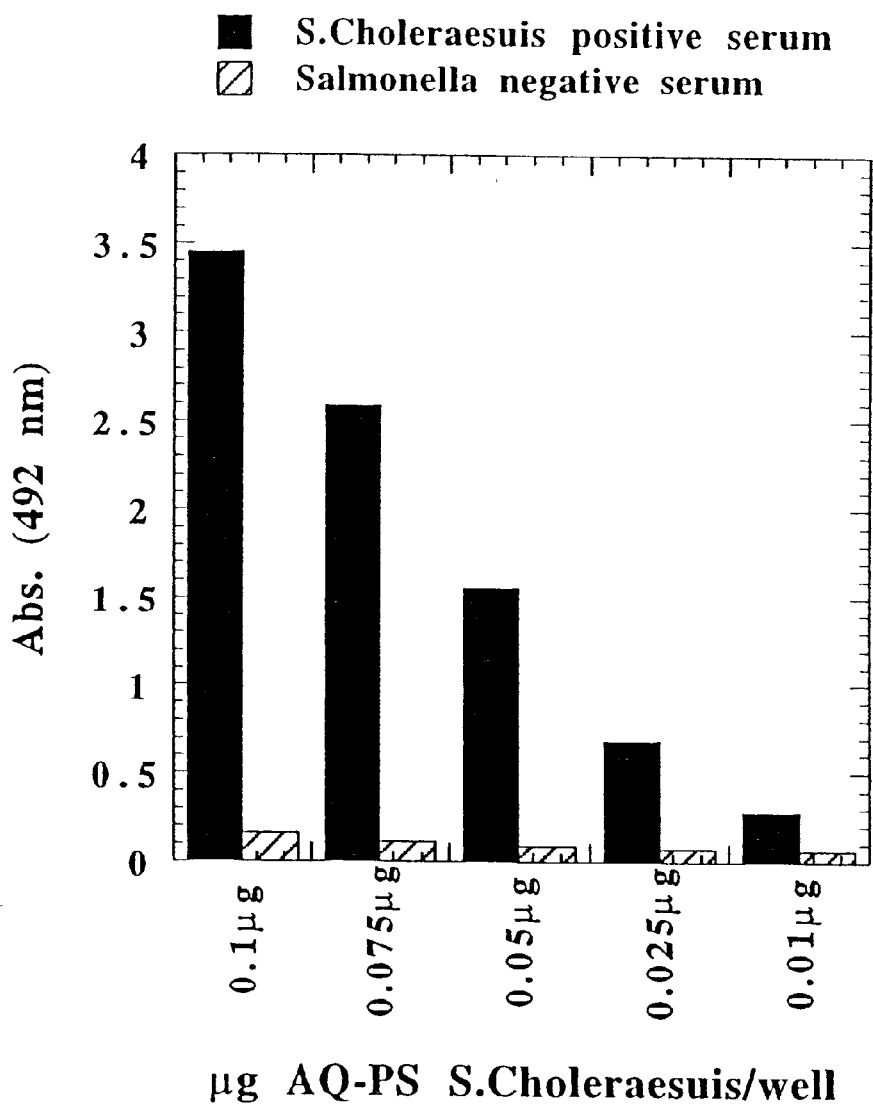
FIG. 16: Effect of AQ-PS (*Salmonella Choleraesuis*) concentration on photocoupling efficiency.

FIG. 15 shows a typical result using a AQ-PS derived from Salmonella Typhimurium and FIG. 16 shows a typical result using a AQ-PS derived from Salmonella Choleraesuis.

EXAMPLE 19

Figure 17:
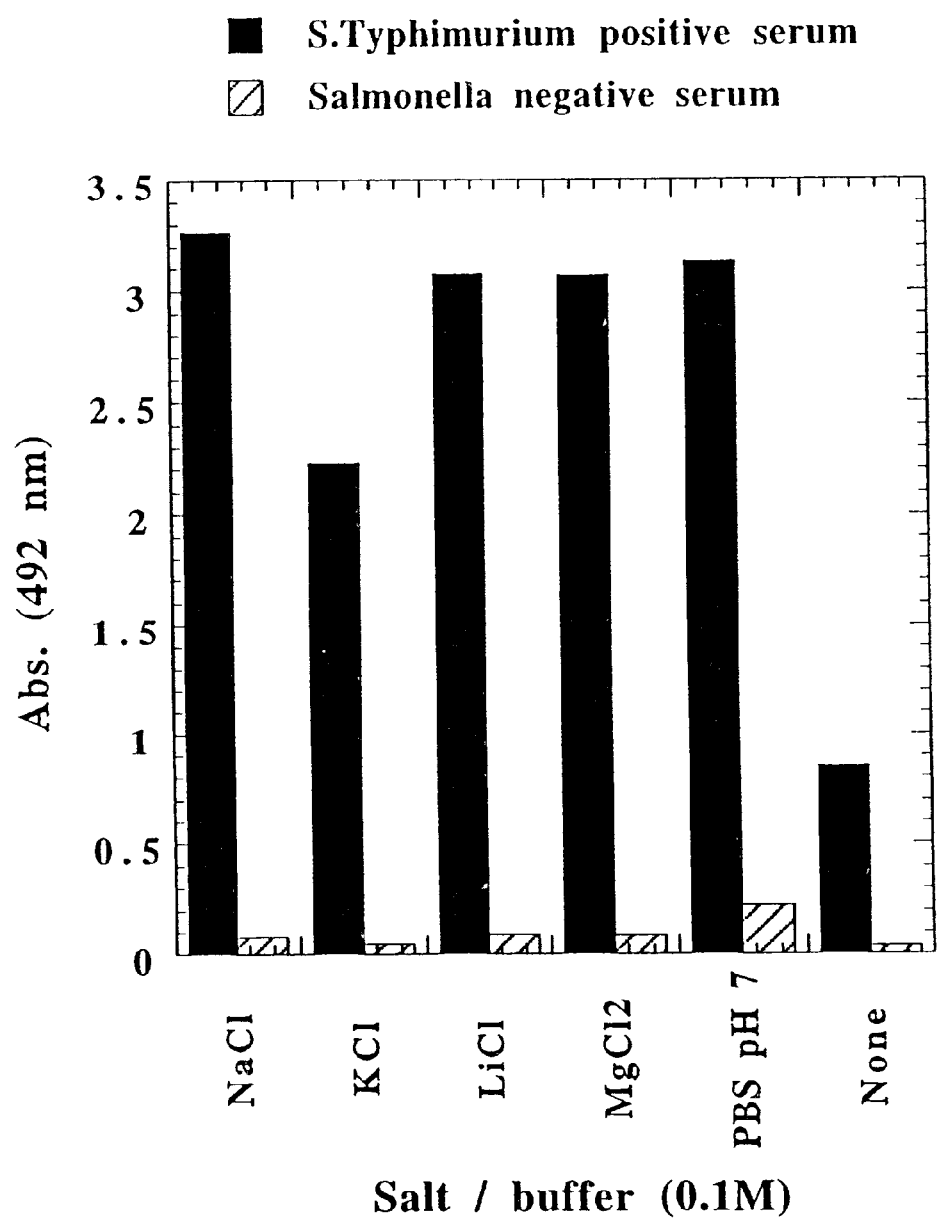
FIG. 17: Effect of inorganic salts and pH on photocoupling efficiency of AQ-PS (*Salmonella Typhimurium*).
Figure 18:
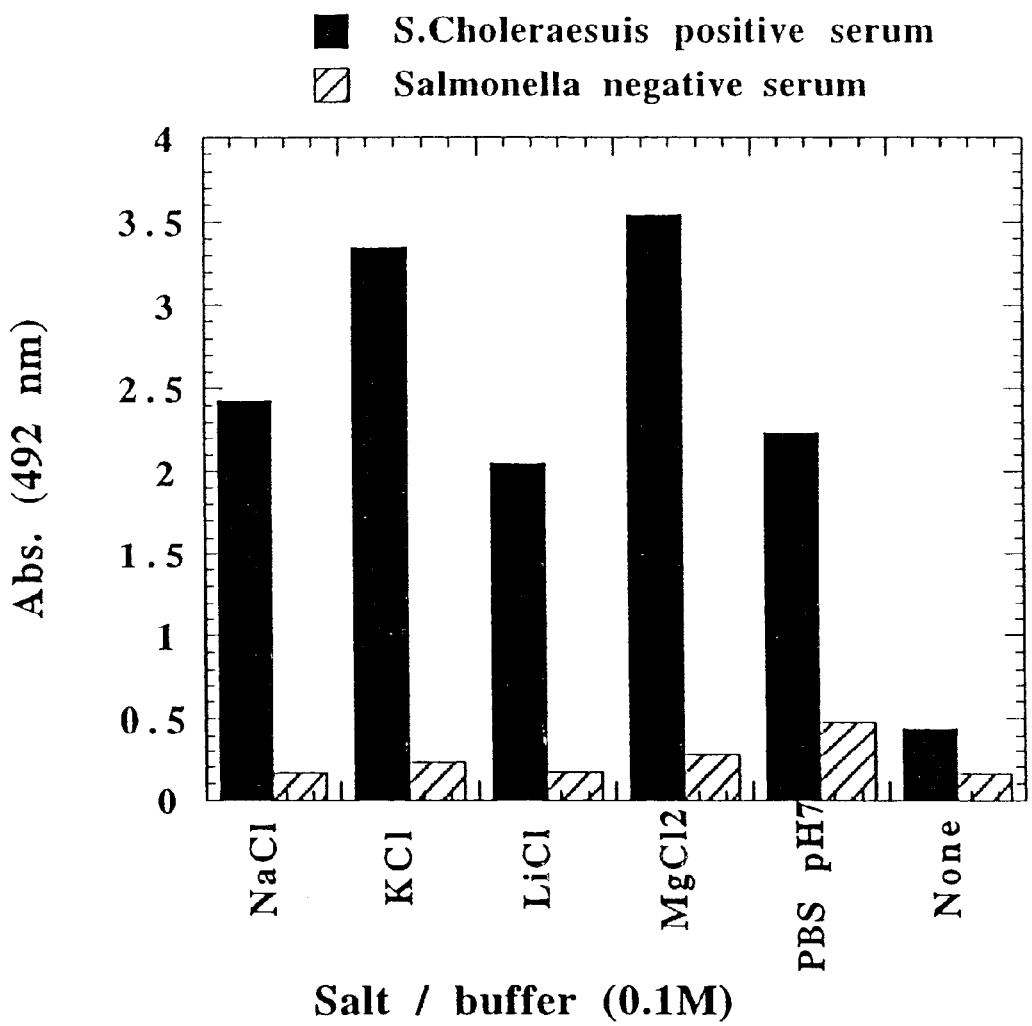
FIG. 18: Effect of inorganic salts and pH on photocoupling efficiency of AQ-PS (*Salmonella Choleraesuis*).

Effect of Inorganic salts and pH on photocoupling efficiency of AQ-PS/AQ-LPS conjugates Make the following buffer and salt solutions using demineralised water: 0.1M NaCl, 0.1 M KCl, 0.1 M LiCl, 0.1 M $MgCl_2$ and PBS pH 7.2. Make a stock solution of AQ-PS conjugate derived from Salmonella Typhimurium and Salmonella Choleraesuis as described in Example 17 and dilute each conjugate into separate tubes containing the different buffer and salt solutions to a final concentration of 5 μg/mL Salmonella Typhimurium and 10 μg/mL for Salmonella Choleraesuis. As reference make two solutions of the conjugates in demineralised water as controls. Add the individual solutions of Salmonella Typhimurium conjugates to column 1–6 of a polystyrene microplate (100 μl/well) and the Salmonella Choleraesuis conjugates to column 7–12 (100 μl/well). Place the microplate below the UV-light source and irradiate for 20 min. Following UV-irradiation aspirate the plate, wash with demineralised water (4×300 μl) and assay directly without drying. Add Salmonella Typhimurium positive reference pig sera diluted in PBS. Tween, BSA (1:400) to each well of rows A1–C6, Salmonella Typhimurium negative reference pig sera diluted in PBS, Tween, BSA (1:400) to each well of rows D1–F6, Salmonella Choleraesuis positive pig reference sera diluted in PBS, Tween, BSA (1:400) to each well of rows A7–C12, Salmonella Choleraesuis negative reference pig sera diluted in PBS, Tween, BSA (1:400) to each well of rows D7–F12, and PBS, Tween, BSA alone in rows G and H (100 μl/well). Incubate at room temperature with gentle agitation for 60 min., aspirate and wash all wells with PBS-Tween (3×300 μl) and add a HRP-labelled rabbit anti swine IgG (DAKO, PO164) diluted in PBS, Tween, BSA (1:2000) to each well from A1 to G12. Incubate for 60 at room temperature with gentle agitation, aspirate the wells and add OPD-substrate solution to each well of the plate (100 μl/well). Incubate the plate for 20 min. in the dark and stop the enzyme reaction by the addition of 0.5 M $H_2SO_4$ (100 μl/well). Read the results on a ELISA reader at 492 nm. FIG. 17 shows a typical result using a AQ-PS derived form Salmonella Typhimurium and FIG. 18 shows a typical result using a AQ-PS derived from Salmonella Choleraesuis.

EXAMPLE 20

Effect of irradiation time on photocoupling efficiency of AQ-PS/AQ-LPS conjugates The AQ-PS/AQ-LPS from Salmonella Typhimurium or Salmonella Choleraesuis is immobilised onto the microplates in order to determine the UV irradiation time to immobilise the conjugates. A diluted solution of AQ-PS/AQ-LPS conjugate (Salmonella Typhimurium and Salmonella Choleraesuis) diluted in 0.1M $MgCl_2$ is added to the plate. As negative control 0.1 M MgCl is added to the plate. The plate (strips) are UV irradiated for different time periods. Following UV-irradiation the plate is washed with demineralised water (4×300 μl) and assayed directly without drying. Salmonella Typhimurium positive pig sera and Salmonella Choleraesuis positive pig sera diluted in PBS-Tween (1:400) is added to the plate (100 μl/well). The plate is incubated at room temperature with gentle agitation for 60 min. The plate is washed 3 times with PBST (300 μl/well). As a secondary antibody rabbit anti-mouse lg conjugated to HRP (PO260, Dako) diluted 1:2000 in PBST is added to the plate. The plate is incubated for 1 hour with agitation. The plate is washed 3 times with PBST (300 μl/well). An OPD-$H_2O_2$ solution is added to the plate (100 μl/well). The plate is incubated for 20 min in the dark. The enzyme reaction is stopped by addition of 0.5M sulphuric acid (100 μl/well). The plate is read at 492 nm in an ELISA reader.

Figure 19:
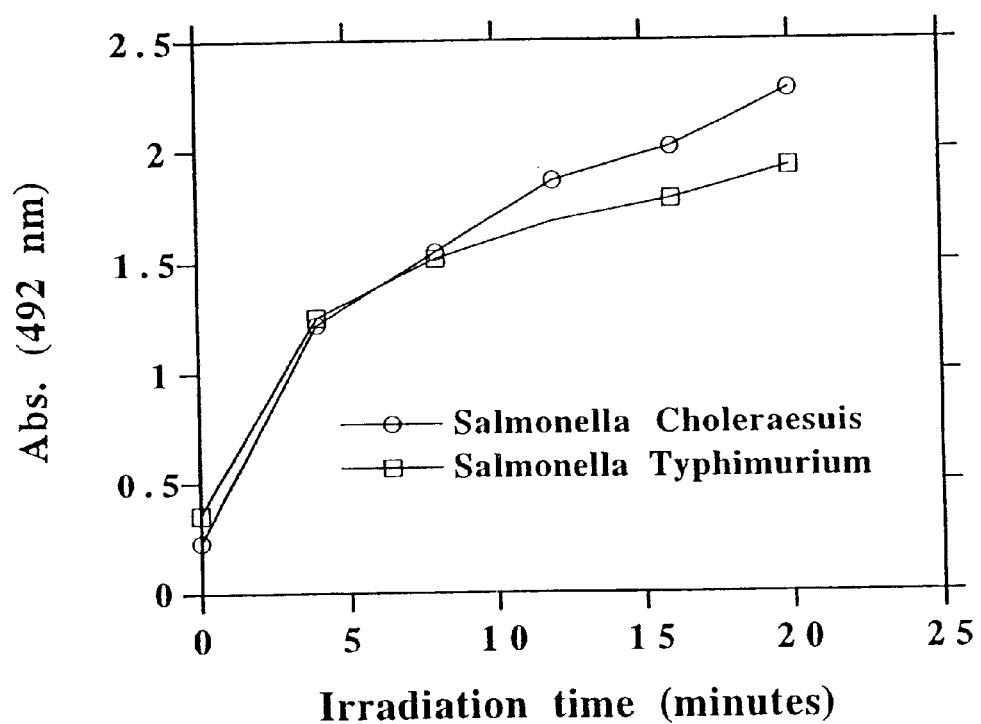
FIG. 19: Effect of irradiation time of AQ-PS (*Salmonella Typhimurium*) and of AQ-PS (*Salmonella Choleraesuis*) on photocoupling efficiency.

FIG. 19 shows a typical result using an AQ-PS conjugate derived from Salmonella Typhimurium and an AQ-PS conjugate derived from Salmonella Choleraesuis.

EXAMPLE 21

Serological test of pig sera on photocoupled AQ-PS derived from Salmonella Typhimurium PS from Salmonella Typhimurium conjugated to AQ is immobilised onto polystyrene microplates by the following method. The Salmonella Typhimurium PS-AQ conjugate is dissolved in ultrapure water. The solutions should be omitted from light. An aliqeuot of the Salmonella Typhimurium PS-AQ conjugate solution is further diluted in 0.1M $MgCl_2$ in order to obtain an optimal concentration. The diluted solution of Salmonella Typhimurium PS-AQ is added to the microplates (100 μL/well). The plates are irradiated in UV light for 20 minutes. After irradiation the plates are washed be the following procedure. The Salmonella Typhimurium PS-AQ conjugate solution is discharged and 300 μL of water is added using a washer. The microplates are subsequently washed 3 times in water (3×300 μL). The microplates are dried at 37° C. for 30 minutes. The microplates are allowed to equilibrate to room temperature for 15 minutes before packing or further use. The plates should be stored at room temperature. For serological use sera and/or meat juice samples from swine are investigated. The ELISA procedure used is an indirect ELISA as followed. An appropriate panel of reference sera is tested on each plate parallel to the specimen samples. Specimen samples or reference sera (100 μL/well) diluted in PBS, Tween, BSA, are added to each well. The plate is incubated for one hour with gentle agitation. The plate is washed in PBS, Tween (3×300 μL). Secondary antibody conjugated to HRP (rabbit anti-swine IgG HRP, PO164, Dako) (100 μL/well) diluted in PBS, Tween, BSA, is added to each well. The plate is incubated for one hour with gentle agitation. The plate is washed in PBS, Tween (3×300 μL). OPD solution (100 μL/well) is added to the plate. The plate is incubated for 20–25 minutes, depending on how fast the controls reaches the appropriate OD values. The enzyme reaction is stopped by addition of 100 μL of 0.5 M sulphuric acid. The plate is shaken manually and read at 492 nm on an ELISA reader.

Figure 20:
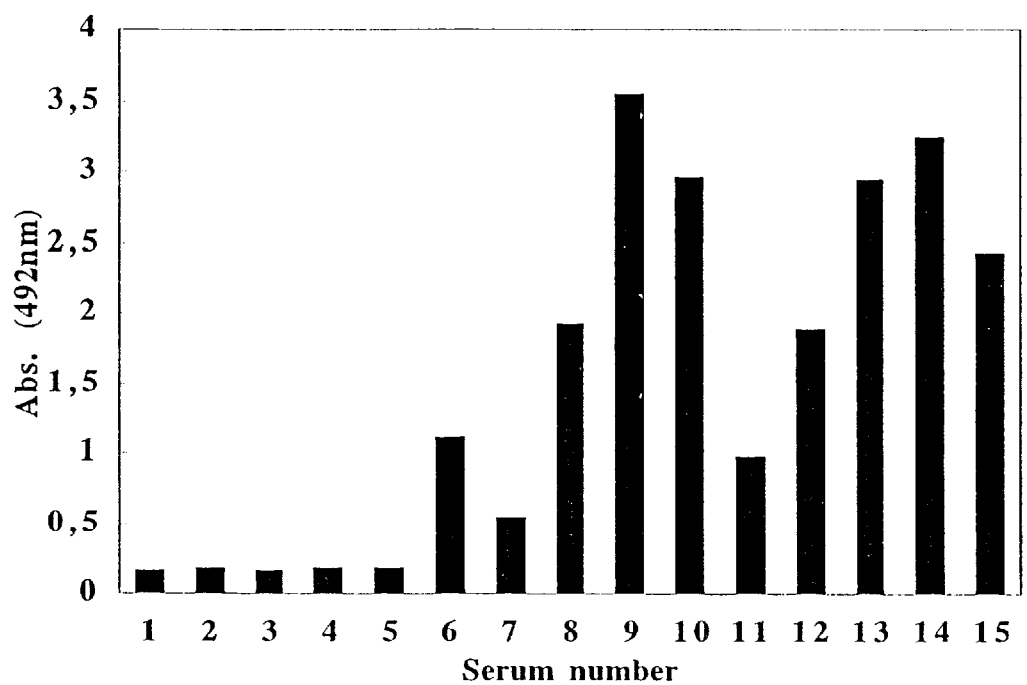
FIG. 20: Serological test (indirect ELISA) of pig sera on photocoupled AQ-PS (*Salmonella Typhimurium*). Sera 1 to 5: sera without any history of Salmonella (negative). Sera 6 to 15: sera from experimentally infected pigs infected with *Salmonella Typhimurium* (positive).

The results are shown in FIG. 20. As seen in the figure sera 1–5 are Salmonella negative while sera 6–15 are positive for Salmonella Typhimurium.

EXAMPLE 24

Figure 21:
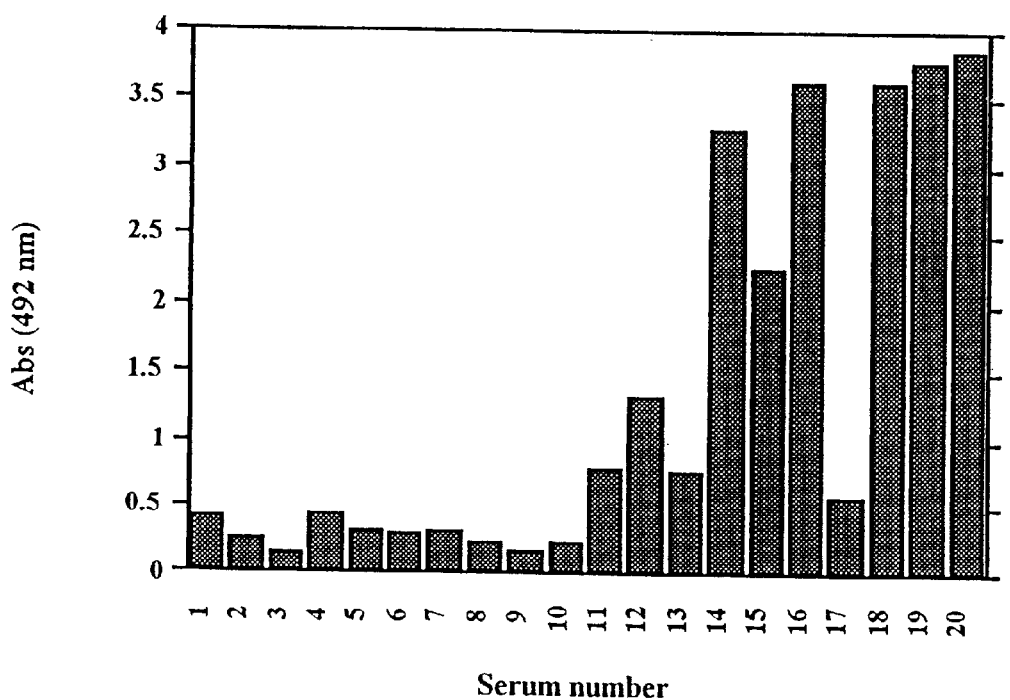
FIG. 21: ELISA on photocoupled mixture of AQ-PS from *Salmonella Typhimurium* and *Salmonella Choleraesuis*. Samples 1–10: Negative control sera. Samples 11–20: Positive sera from experimentally *Salmonella Typhimurium* infected pigs.

Serological tests using covalently coupled lipopolysaccharide polysaccharides: A mixture of coupled Salmonella polysaccharides In a comparitive experiment plates were coated with a mixture of Salmonella Typhimurium and Salmonella Choleraesuis polysaccharides as described above (covalent mix-ELISA) and compared to plates conventionally coated ("Mix-ELISA" (Nielsen 1995)) with whole LPS from the same two Salmonella serotypes. Four Salmonella Typhimurium positive, two Salmonella Infantis positive and one Salmonella- negative sera were used as reference sera to calibrate the OD-readings from each ELISA plate, exactly as described previously (Nielsen (1995), see below. The covalent Mix-ELISA was performed as the previously published mix-ELISA protocol (Nielsen et al. 1995), except that the blocking step (with bovine serum albumin, BSA) was omitted. Sera were diluted 1:400 in PBS, Tween, BSA. Duplicates of 100 1 of each serum was applied and incubated for 1 h at room temperature without agitation. The plates were then washed three times in PBS, T and subsequently incubated with HRP-conjugated rabbit anti swine IgG (PO164, DAKO) diluted 1:3000 in PBS, Tween, BSA for 1 h at room temperature. The plates were then washed as before, and 100 μL OPD substrate solution was added to each well and incubated 10–15 min. The reaction was stopped with 100 μL H₂SO₄ and the optical density was read at 490 nm, subtracting 650 nm (background correction). To test the AQ-PS-coated plates a panel of 20 sera with known reactivity in the mix-ELISA system were used (20 sera from pigs from multiplying herds). A typical result is shown in FIG. 21. When using a cut-off at 10 OD %, all of the sera remained in the same group of positives or negatives, when being tested in the AQ-PS-ELISA and the mix-ELISA, respectively. The OD-level of the low responding samples correlated well between the two systems. For the positive samples a slight reduction was observed in the AQ PS-ELISA for some of the samples, but this feature varied from day to day.

EXAMPLE 25

Reproducibility of photocoupled mixed AQ-PS derived from Salmonella Typhimurium and Salmonella Choleraesuis The reproducibility of the AQ-PS immobilised microplates has been investigated over a longer period. Microplates have been immobilised with mixed AQ-PS derived from Salmonella Typhimurium and Salmonella Choleraesuis as described above. Reference sera have been added to the plates in 16 duplicates on each plate. This procedure have been repeated on four plates each day over a period of four days. The results were normalised against a control reference serum. Intraplate variation was measured to 7.7% while interplate variation was measured to 5.1%

EXAMPLE 26

Figure 22:
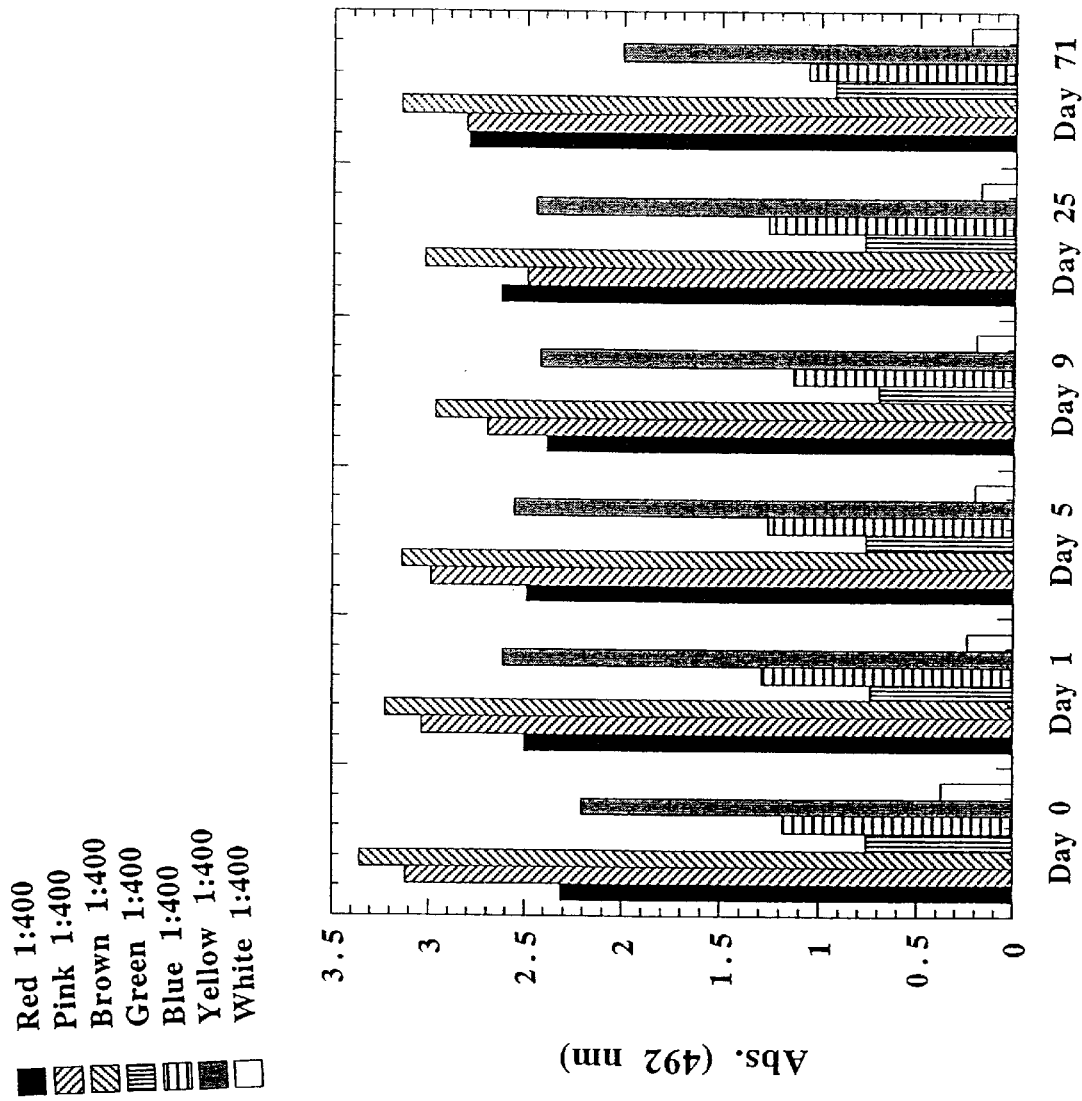
FIG. 22: Storage stability of photocoupled mixed AQ-PS (*Salmonella Typhimurium* and *Salmonella Choleraesuis*). Sera: White: sera without any history of Salmonella (negative); Red, Pink, Brown, Green: sera from experimentally infected pigs infected with *Salmonella Typhimurium* (positive); Yellow, Blue: sera from experimentally infected pigs infected with *Salmonella Infantis* (positive).

Storage stability of photocoupled mixed AQ-PS derived from Salmonella Typhimurium and Salmonella Choleraesuis The storage stability of the Salmonella Typhimurium and Salmonella Choleraesuis mixed AQ-PS ELISA plates is a important factor to investigate. A long storage stability provides a plate that is independent of coating procedures prior to use and provides a plate that shows minimal variations within the same batch as well as between batches. The stability of the PS-AQ immobilised microplates has been investigated over a period of several months. Plates were prepared as described in Example 23 and stored at room temperature in the dark and then the plates were tested using a panel of reference sera directed against Salmonella Typhimurium and Salmonella Choleraesuis O-antigens in PS/LPS over a period of 71 days. The results are seen in FIG. 22. As seen in FIG. 22, the plates were stable for at least 71 days.

EXAMPLE 27

Detection of infection levels of swing herds using a serological test based on photocoupled mixed AQ-PS derived from Salmonella Typhimurium and Salmonella Choleraesuis The microplates photocoupled with mixed AQ-PS derived from Salmonella Typhimurium and Salmonella Choleraesuis have been investigated for serological use. For serological surveillance of swine herds it is of great importance to achieve a standardised microplate with minimal variations in order to achieve a reliable and reproducible response in each assay. To obtain this, one has to produce plates with the previously described qualities.

A panel of sera from 59 conventional swine herds (10 sera from each herd) was investigated using a photocoupled mixture of Salmonella Typhimurium and Salmonella Choleraesuis PS as described in Example 26. The result of this analysis was compared to the result of the analysis of the same samples in a conventionally coated "Mix-ELISA" (Nielsen 1995) using LPS from the same two types of Salmonella. The herds were classified as having a low prevalence of salmonella based on the Mix-ELISA and based on the principles of the Danish Salmonella surveillance program (Mousing J, Jensen P T, Halgaard C, Bager F, Feld N, Nielsen B, Nielsen J P, Bech-Nielsen S:1997. Nation-wide Salmonella enterica surveillance and control in Danish slaughter swine herds. Prev. Vet. Med. 29:247–261.)

The ELISA procedure used is an indirect ELISA as followed. An appropriate panel of reference sera are tested on each plate parallel to the specimen samples. Specimen samples or reference sera (100 µL/well) diluted in PBS, Tween, BSA, are added to each well. The plate is incubated for one hour (the use of agitation during incubation may enhance the P/N ratio between positive and negative samples). The plate is washed in PBS, Tween (3×300 µL). Secondary antibody conjugated to HRP (rabbit anti-swine IgG HRP, PO164, Dako) (100 µL/well) diluted in PBS, Tween, BSA (1:2000) is added to each well. The plate is incubated for one hour with mild agitation. The plate is washed in PBS, Tween (3×300 µL). OPD solution (100 µL/well) is added to the plate. The plate is incubated for 20–25 minutes, depending on how fast the controls reaches the appropriate OD values. The enzyme reaction is stopped by addition of 100 µL of 0.5 M sulphuric acid. The plate is shaken manually and read at 492 nm on an ELISA reader. Only four out of the 590 samples were positive in the photocoupled assay, maintaining the classification of all herds as having a low Salmonella prevalence as also found with the conventional "mix-ELISA".

EXAMPLE 28

Detection of Salmonella Typhimurium bacteria using a competitive ELISA test based on photocoupled mixed AQ-PS derived from Salmonella Typhimurium and Salmonella Choleraesuis The microplates photocoupled with mixed AQ-PS derived from Salmonella Typhimurium and Salmonella Choleraesuis can be used as an antigen ELISA for detection of Salmonella bacteria or Salmonella antigen. Detection of Salmonella bacteria in foods or environmental has a great potential. Detection of Salmonella bacteria can be accomplished by use of the photocoupled mixed AQ-PS Salmonella Typhimurium and Salmonella Choleraesuis as a competitive ELISA by the following procedure.

Bacteria samples are added to the plates in two fold dilutions, diluted in PBS (50 µL/well). As a control PBS is added (without any bacteria samples) to the plates (50 µL/well). A monoclonal antibody (50 µL/well) diluted in PBS, Tween, BSA, directed against the relevant Salmonella serotype is added to the plate. As a negative control the monoclonal antibody is added to a well with PBS. As a positive control PBS, Tween, BSA is added to a well with PBS. The plate is incubated for one hour with gentle agitation. The plate is washed is PBS, Tween (3×300 µL). Secondary antibody conjugated to HRP (rabbit anti-mouse IgG HRP, PO260, Dako) (100 µL/well) diluted in PBS, Tween, BSA, is added to each well. The plate is incubated for one hour using agitation. The plate is washed in PBS, Tween (3×300 µL), make sure that all wells are filled during each wash. OPD solution (100 µL/well) is added to the plate. The plate is incubated for 20–25 minutes, depending on how fast the controls reaches the appropriate OD values. The enzyme reaction is stopped by addition of 100 µL of 0.5 M sulphuric acid. The plate is shaken manually and read at 492 nm on an ELISA reader. The wells with monoclonal antibody (are calculated as 100% response). The wells with PBS, Tween, BSA (are calculated as 0% response). The OD response of the wells with bacteria samples are calculated in relation to the positive and the negative controls. The decrease of the response is proportional to the increase in positivity of the sample. From the titration curve the titre is calculated. The titre is the dilution factor of the bacterial solution leading to a 50% decrease in the OD-value compared to the OD-value obtained without competing antigen (100% response).

EXAMPLE 29

Conjugation of biotin to PS derived from Salmonella Typhimurium

Make up following coupling buffer and freshly prepared solutions of reagents:
Solution 1: 1 mM N-hydroxy succinimide in DMSO (6 mg N-hydroxy succinimide dissolved in 50 mL DMSO).
Solution 2: 2 mM WSC in ultrapure water (9.6 mg WSC dissolved in 25 mL water).
Solution 3: 2 mM of biotin-amine in ultrapure water (dissolve 19 mg in 25 mL water).
Buffer: Sodium hydrogen carbonate buffer, pH 8.0 (sodium hydrogen carbonate (8.4 g) is dissolved in ultrapure water and the pH adjusted to 8.0 with 1M aqueous HCl).

Figure 23:
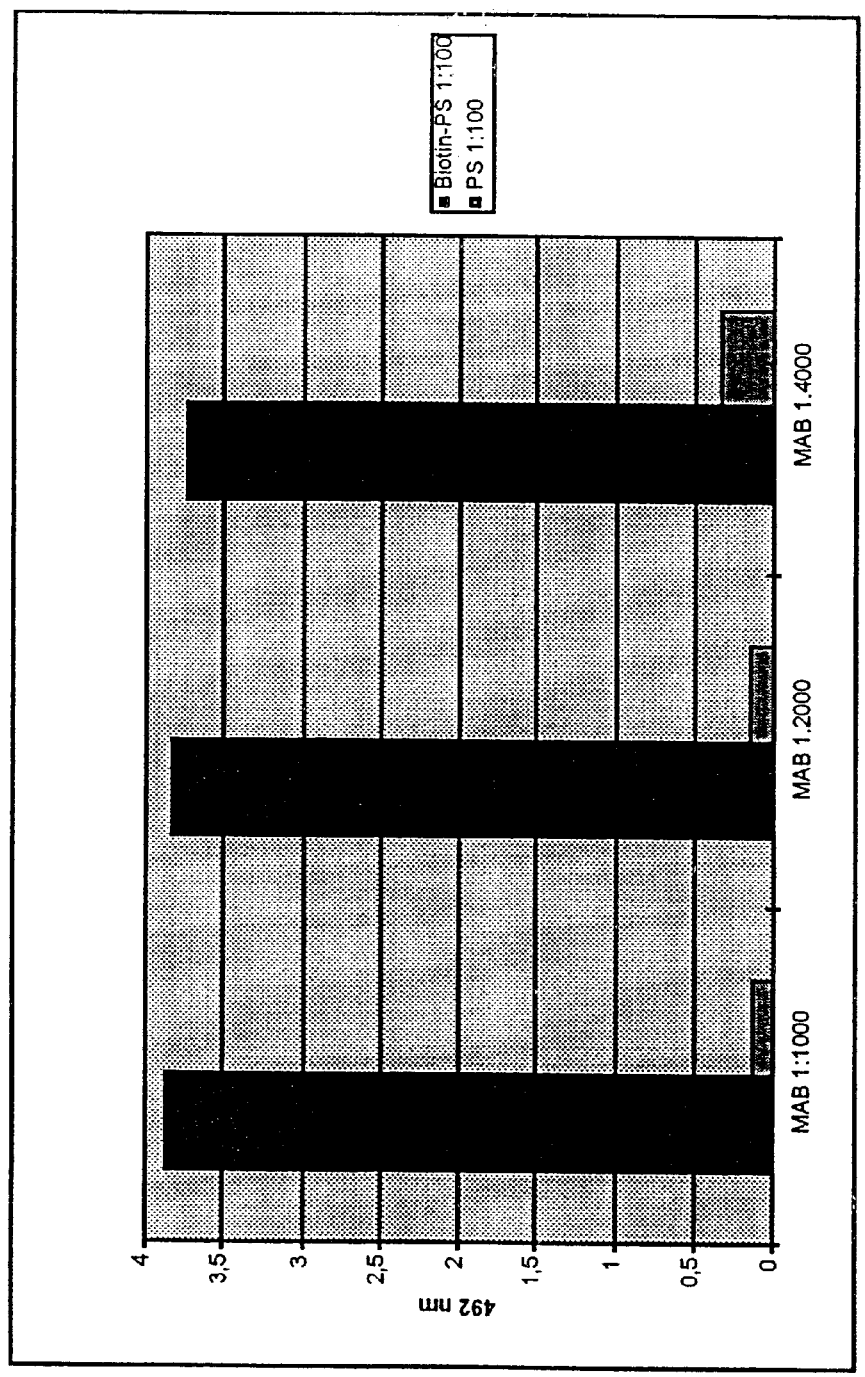
FIG. 23: Indirect ELISA of PS and biotin-PS conjugates (*Salmonella Typhimurium*) on streptavidin coated plates. (Left columns: Biotin-PS; Right columns: PS.)

The resultant clear solution is stirred overnight at 4° C. The reaction mixture is subsequently dialysed against ultrapure water for three days, changing the ultrapure water every day. The PS-biotin conjugate is finally lyophilised overnight. The lyophilised PS-biotin conjugate is dissolved in ultrapure water to a final concentration of 1 mg/mL. This stock solution of PS-biotin conjugate have a long term stability (more than 3 months) when stored at 4° C. protected from direct light. The stock solutions are diluted in PBS pH 7.2, 1:100 and 1:400. The diluted PS-biotin solutions are added to a microplate (100 µl/well) coated with streptavidin (Pierce). As a control diluted PS solutions (1:100 and 1:400 in PBS) are added to the microplate (100 µl/well). The plate is incubated for 1 hour with agitation. The plate is washed 3 times with PBST (300 µl/well). A monoclonal antibody against Salmonella Typhimurium LPS (O-chain) (S97, HyTest Ltd.) is added to the plate in a two-fold dilution (diluted in PBST) 100 µl/well. The plate is incubated for 1 hour with agitation. The plate is washed 3 times with PBST (300 µl/well). As a secondary antibody rabbit anti-mouse Ig conjugated to HRP (PO260, Dako) diluted 1:2000 in PBST is added to the plate. The plate is incubated for 1 hour with agitation. The plate is washed 3 times with PBST (300 µl/well). An OPD-H$_2$O$_2$ solution is added to the plate (100 µl/well). The plate is incubated for 20 min in the dark. The enzyme reaction is stopped by addition of 0.5M sulphuric acid (100 µl/well). The plate is read at 492 nm in an ELISA reader. The results are seen in FIG. 23. As seen in FIG. 23 only the biotin conjugated PS binds to the streptavidin plate.

EXAMPLE 30

Clinical tests using covalently coupled lipopolysaccharide polysaccharides: Coupled Actinobacillus pleuropneumoniae serotype 5b polysaccharides Polysaccharides derived from *Actinobacillus pleuropneumoniae* serotype 5b (App5 b) as described above (Example 10) are derivatised with AQ as described for salmonella PS in Example 12a, and subsequently coupled to PolySorp immunoplates from Nunc as described above (Example 17). The microtiter plates were covalently coupled with the APP 5b PS-AQ conjugate in a two-fold dilution from 500 ng to 0.98 ng PS-AQ per well. A positive and a negative serum for APP 5b diluted 1:400 in PBS-T was applied to the plates. The plates were incubated for 1 hour. The plates were washed 3 times in PBS-T and subsequently incubated with a secondary antibody (rabbit anti-swine Ig HRP-conjugated). The plates were incubated for 1 hour and subsequently washed 3 times in PBS-T. The plates were developed with OPD.

Figure 24:
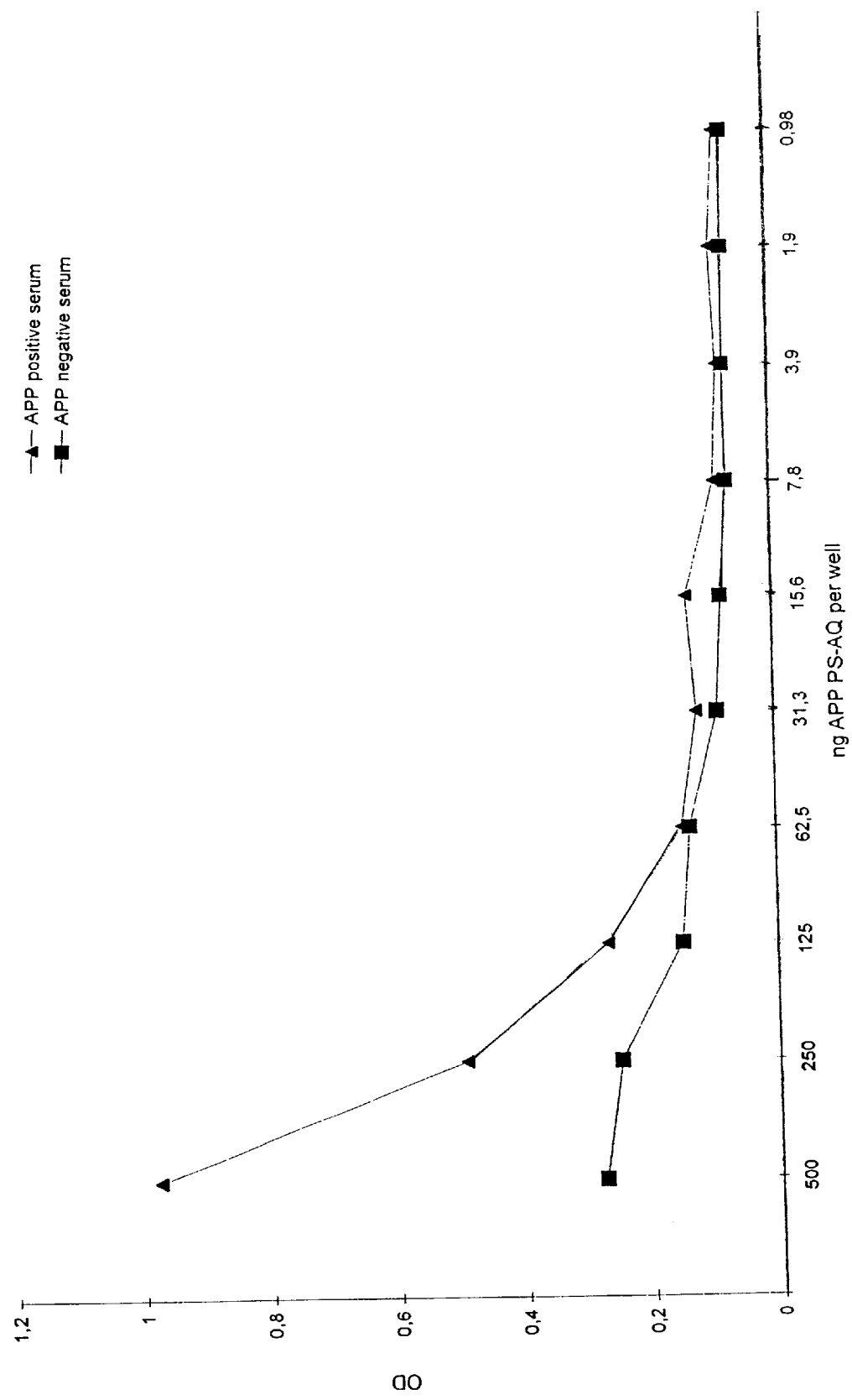
FIG. 24: Two-fold titration of the APP5b PS-AQ conjugate, starting from 500 ng PS-AQ per well. The plate was incubated with an APP5b positive swine serum and a negative serum (SPF serum) diluted 1:400 in PBST.

The results are shown in FIG. 24. The Figure shows that the *Actinobacillus pleuropneumoniae* serotype 5b lipopolysaccharide derived polysaccharide can be conjugated to AQ and covalently coupled to a microplate surface. The antigenicity was retained as the PS-AQ antigen coated plates showed similar response to LPS passively coated plates. Actinobacillus is a Gram-negative bacteria of the HAP family and is therefore tacomomically not closely related to Salmonella strains. This indicates that LPS from Gram-negative bacteria in general may be successfully converted to PS-AQ conjugates.

EXAMPLE 31

Clinical tests using covalently coupled lipopolysaccharide polysaccharides: Coupled *Actinobacillus pleuropneumoniae* serotype 6 polysaccharides Polysaccharides derived from *Actinobacillus pleuropneumoniae* serotype 6 as described above (Example 10) are derivatised with AQ as described for Salmonella PS in Examples 12–13 and subsequently coupled to Polysorp immunoplates from Nunc as described above (Example 17). This surface is compared to a conventional surface prepared by adsorbing whole LPS from the same *Actinobacillus pleuropneumoniae* (Ap) strain in a competition ELISA using a polyclonal antibody as detection antibody and blockade by well-defined pig sera. Briefly, the ELISA is performed as follows: The optimal concentration of the Ap6 LPS antigen, serum and enzyme conjugate are determined by checkerboard titrations in ELISA plates. The microplates are coated with LPS diluted 1:10.000in PBS and incubated overnight at 4° C. The plates are blocked with PBS with 0.05% Tween 20 and with 1% bovine serum albumin (PBS, T, BSA) for 30 min at room temperature (RT). Test sera are diluted 1:10 in PBS, T, BSA and added to the wells in duplicate and incubated for 1 h at RT. Without emptying the plates rabbit serum diluted 1:8000 is added for 30 min at RT. Afterwards the plates are incubated with peroxidase-conjugated swine anti-rabbit immunoglobulin (Dako, Copenhagen, Denmark) diluted 1:1000 in PBS, T, BSA. The substrate-dye solution o-phenylenediamine-$H_2O_2$ is allowed to react for 15 min and the reaction is stopped by the addition of 0.5 M $H_2SO_4$. The optical density at 490 nm is measured with 650 nm as the reference. The optical density of the rows containing PBS, T, BSA without serum is used for calculation of the percent inhibition by the individual sera. The dilution and incubation time for the test serum and the rabbit serum are adjusted to give 0–25% inhibition with negative sera and 80–100% with positive serum.

The results are expected to show that the Ap-derived polysaccharide can be coupled covalently to the microplate surface while retaining its antigenicity and showing a blocking behaviour comparable to or better than conventionally non-covalently coated whole LPS.

EXAMPLE 32

Conjugation of $H_2N$-$(CH_2)_3$-NHCO-AQ . HCl to KDO

KDO (10 mg, 40 µmol), $H_2N$-$(CH_2)_3$-NHCO-AQ.HCl (7 mg, 20 µmol) and BOP (21 mg, 48 µmol) was dissolved in DMSO. Then, triethyl amine (17 µl, 120 µmol) was added and the clear solution stirred at room temperature for 60 hours. Water (40 mL) was added to the reaction mixture followed by freeze drying. The solid product mixture was redissolved/resuspended in water (1 mL) and added to a SeppPak C18 column (1 mL) that had previously been equilibrated with acetonitrile (7 mL) and water (7 mL). The column was eluted with water (10 mL) and then water/acetonitrile (10 mL, 1:1 V/V). The first aqueous fraction contained mainly excess KDO and other impurities, while the second water/acetonitrile fraction contained the AQ-KDO conjugate. TLC (1-butanol/acetic acid/water 4:1:1): $R_f$=0.33. MS (MALDI-TOF): 545.8 (MH$^+$+$H_2O$).

EXAMPLE 33

A method for estimating the number of a specific bacteria, serotyping or bacteria or antigen (LPS/PS) detection is established by use of AQ-PS immobilised microplates.

A solution of bacteria or an antigen solution (LPS/PS) is added to the plates in a two fold dilution (50 µL/well). A monoclonal antibody against Salmonella Typhimurium or Salmonella Choleraesuis diluted in PBS, Tween, BSA (50 µL/well) is added to the plate. The plate is incubated for one hour with mild agitation. The plate is washed 3 times with PBS, Tween (300 µL/well). A rabbit anti-mouse IgG conjugated to HRP (PO260, Dako) diluted in PBS, Tween, BSA (100 µL/well) is added to the plate. The plate is incubated for one hour with mild agitation. The plate is washed 3 times with PBS, Tween (300 µL/well). An OPD-solution is added to the plate (100 µL/well). The plate is incubated for 20 min in the dark. The reaction is stopped by addition of 0.5M $H_2SO_4$ (100 µl/well). The plate is read at 492 nm in an ELISA reader. This method provides the detection of small amounts of bacteria in biological fluids and provides the determination of a bacteria serotype.

What is claimed is:

1. A diagnostic assay comprising:
   providing a solid surface substrate, the substrate comprising a bacterial lipopolysaccharide on the substrate surface, the polysaccharide having a keto-carboxy group or ketal or hemiketal group corresponding thereto,
   wherein a covalent bond is formed between the carboxy group of the polysaccharide and a reporter molecule, thereby forming a polysaccharide-reporter molecule conjugate, the reporter molecule comprising a recognition/substrate site; and
   contacting the substrate with a biological fluid test sample to determine the presence of a Gram-negative bacteria in the sample.

2. The assay of claim 1 wherein the test sample is suspected of containing antibodies against Salmonella spp.

3. The assay of claim 1 wherein the test sample is suspected of containing antibodies against Actinobacillus spp.

4. The assay of claim 1 further comprising determining whether the test sample contains antibodies against a Gram-negative bacteria.

5. The assay of claim 1 further comprising determining whether the test sample contains antibodies against Salmonella spp.

6. The assay of claim 1 further comprising determining whether the test sample contains antibodies against Actinobacillus spp.

7. The assay of claim 1 wherein the polysaccharide is immobilized on the substrate by a covalent bond between a carboxy group of the polysaccharide and a chemical functionality linked to the substrate surface.

8. The assay of claim 1 wherein the polysaccharide is covalent bonded to the solid surface through a coupling agent.

9. The assay of claim 1 wherein the bacterial lipopolysaccharide is derived from a bacteria selected from the group consisting of enterobacteria, respiratory, urogenitial bacteria or a neuropathogenic bacteria.

10. The assay of claim 1 wherein the bacteria is an enterobacteria.

11. The assay of claim 1 wherein the bacteria is selected from the group consisting of *Escherichia coli*, Salmonella Typhimunium, Salmonella Cholereasuis, and Salmonella Enterica.

12. The assay of claim 1 wherein the bacteria is a respiratory bacteria.

13. The assay of claim 1 wherein the bacteria is Actinobacillus sp bacteria.

14. The assay of claim 1 wherein the bacteria is *Actinobacillus pleuropneumoniae, Haemophilius somnus, Pasteurella haemolytica, Pasteurella multocida, Haemophilius parasuis* or Mannheimia sp.

15. The assay of claim 1 wherein the reporter groups comprises a reporter part presenting the recognition/substrate site and a linker part for linking the reporter part to the polysaccharide.

16. The assay of claim 1 wherein the polysaccharide-reporter molecule conjugate has the formula PS'-C(=O)-N(RN)-F-L-R, where PS'-C(=O) is the polysaccharide, N(RN)-F is the group directly involved in the covalent link between the polysaccharide and the reporter molecule, RN designates hydrogen or $C_{1-4}$alkyl, L is the linker part of the reporter molecule, and R is the reporter part of the reporter molecule.

17. The assay of claim 16 wherein —N(RN)-F- designates amino, aniline, hydrazido, semicarbazido, thiosemicarbazido, or hydrazino.

18. The assay of claim 16 wherein —N(RN)-F- is amino.

19. The assay of claim 16 wherein L designates a biradical selected from the group consisting of $C_{1-20}$alkylene optionally comprising aromatic or mono/polyunsaturated hydrocarbons or cyclic hydrocarbons, oligo-oxyethylenes, oligoamides and oligopeptides.

20. The assay of claim 1 wherein the reporter molecule is a photochemically reactive group.

21. The assay of claim 1 wherein the reporter molecule is a thermochemically reactive group.

22. The assay of claim 1 wherein the reporter molecule is one part of an affinity pair.

* * * * *